United States Patent
Noureldin et al.

(10) Patent No.: US 9,816,759 B2
(45) Date of Patent: Nov. 14, 2017

(54) POWER GENERATION USING INDEPENDENT TRIPLE ORGANIC RANKINE CYCLES FROM WASTE HEAT IN INTEGRATED CRUDE OIL REFINING AND AROMATICS FACILITIES

(71) Applicant: Saudi Arabian Oil Company, Dhahran (SA)

(72) Inventors: Mahmoud Bahy Mahmoud Noureldin, Dhahran (SA); Hani Mohammed Al Saed, Jubail Ind. (SA); Ahmad Saleh Bunaiyan, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 0 days.

(21) Appl. No.: 15/087,503

(22) Filed: Mar. 31, 2016

(65) Prior Publication Data

US 2017/0058718 A1 Mar. 2, 2017

Related U.S. Application Data

(60) Provisional application No. 62/209,217, filed on Aug. 24, 2015, provisional application No. 62/209,147, (Continued)

(51) Int. Cl.
*F01K 25/06* (2006.01)
*F01K 27/02* (2006.01)
(Continued)

(52) U.S. Cl.
CPC .......... *F28D 7/0083* (2013.01); *B01D 3/007* (2013.01); *B01D 3/32* (2013.01); *B01D 51/10* (2013.01);
(Continued)

(58) Field of Classification Search
CPC .......... F01K 25/06; F01K 27/02; F01K 25/08; F01K 3/185; F01K 13/02; F01K 13/00;
(Continued)

(56) References Cited

U.S. PATENT DOCUMENTS 3,995,428 A 12/1976 Roberts
4,024,908 A 5/1977 Meckler
(Continued)

FOREIGN PATENT DOCUMENTS

CN 1844325 10/2006
CN 101424453 5/2009
(Continued)

OTHER PUBLICATIONS

"Organic Rankine Cycle," Choice of the Working Fluid, Wikipedia, published on or before Sep. 2014, 4 pages. http://en.wikipedia.org/wiki/Organic_Rankine_cycle?oldid=628773207.
(Continued)

*Primary Examiner* — Hoang Nguyen
(74) *Attorney, Agent, or Firm* — Fish & Richardson P.C.

(57) ABSTRACT

A power generation system includes four heating fluid circuits thermally coupled to heat sources from sub-units of a petrochemical refining system. The sub-units include a hydrocracking plant, an aromatics plant, and a diesel hydro-treating plant. Subsets of the heat sources includes hydrocracking plant heat exchangers coupled to streams in the hydrocracking plant, aromatics plant heat exchangers coupled to streams in the aromatics plant, and diesel hydro-treating plant heat exchangers coupled to streams in the diesel hydro-treating plant. A power generation system includes three organic Rankine cycles, each including a working fluid that is thermally coupled to at least one heating fluid circuit to heat the working fluid, and an expander to generate electrical power from the heated work-
(Continued)

ing fluid. The system includes a control system to activate a set of control valves to selectively thermally couple each heating fluid circuit to at least a portion of the heat sources.

30 Claims, 23 Drawing Sheets

Related U.S. Application Data filed on Aug. 24, 2015, provisional application No. 62/209,188, filed on Aug. 24, 2015, provisional application No. 62/209,223, filed on Aug. 24, 2015.

(51) Int. Cl.
| | | |
|---|---|---|
| F01K 25/08 | (2006.01) | |
| F28D 7/00 | (2006.01) | |
| C10G 45/02 | (2006.01) | |
| C10G 35/04 | (2006.01) | |
| C10L 3/10 | (2006.01) | |
| C07C 7/08 | (2006.01) | |
| C10G 65/12 | (2006.01) | |
| C10G 33/06 | (2006.01) | |
| B01D 3/00 | (2006.01) | |
| B01D 3/32 | (2006.01) | |
| B01D 51/10 | (2006.01) | |
| B01D 53/047 | (2006.01) | |
| B01D 53/14 | (2006.01) | |
| B01D 53/18 | (2006.01) | |
| B01D 53/34 | (2006.01) | |
| B01D 53/48 | (2006.01) | |
| B01D 53/86 | (2006.01) | |
| B01D 53/96 | (2006.01) | |
| C02F 1/58 | (2006.01) | |
| C10G 45/44 | (2006.01) | |
| C10G 47/00 | (2006.01) | |
| F28F 9/26 | (2006.01) | |
| C10G 65/00 | (2006.01) | |
| F01D 17/14 | (2006.01) | |
| F01K 3/18 | (2006.01) | |
| F01K 13/02 | (2006.01) | |
| H02K 7/18 | (2006.01) | |
| C10G 69/00 | (2006.01) | |
| F01K 13/00 | (2006.01) | |
| F01K 23/06 | (2006.01) | |
| C01B 3/24 | (2006.01) | |
| C10G 45/00 | (2006.01) | |
| C10K 3/04 | (2006.01) | |
| F01K 27/00 | (2006.01) | |
| C02F 101/10 | (2006.01) | |
| C02F 101/16 | (2006.01) | |
| C02F 103/18 | (2006.01) | |
| C02F 103/36 | (2006.01) | |

(52) U.S. Cl.
CPC ........ *B01D 53/047* (2013.01); *B01D 53/1462* (2013.01); *B01D 53/185* (2013.01); *B01D 53/343* (2013.01); *B01D 53/48* (2013.01); *B01D 53/8603* (2013.01); *B01D 53/96* (2013.01); *C01B 3/24* (2013.01); *C02F 1/586* (2013.01); *C07C 7/08* (2013.01); *C10G 33/06* (2013.01); *C10G 35/04* (2013.01); *C10G 45/00* (2013.01); *C10G 45/02* (2013.01); *C10G 45/44* (2013.01); *C10G 47/00* (2013.01); *C10G 65/00* (2013.01); *C10G 65/12* (2013.01); *C10G 69/00* (2013.01); *C10K 3/04* (2013.01); *C10L 3/101* (2013.01); *C10L 3/103* (2013.01); *C10L 3/104* (2013.01); *F01D 17/145* (2013.01); *F01K 3/185* (2013.01); *F01K 13/00* (2013.01); *F01K 13/02* (2013.01); *F01K 23/06* (2013.01); *F01K 23/064* (2013.01); *F01K 25/06* (2013.01); *F01K 25/08* (2013.01); *F01K 27/00* (2013.01); *F01K 27/02* (2013.01); *F28F 9/26* (2013.01); *H02K 7/1823* (2013.01); *B01D 2252/204* (2013.01); *C01B 2203/0233* (2013.01); *C02F 2101/10* (2013.01); *C02F 2101/101* (2013.01); *C02F 2101/16* (2013.01); *C02F 2103/18* (2013.01); *C02F 2103/36* (2013.01); *C10G 2300/202* (2013.01); *C10G 2300/207* (2013.01); *C10G 2300/4006* (2013.01); *C10G 2300/4056* (2013.01); *C10G 2400/04* (2013.01); *C10G 2400/30* (2013.01); *C10L 2290/06* (2013.01); *C10L 2290/541* (2013.01)

(58) Field of Classification Search
CPC ........ F01K 23/06; F01K 23/064; F01K 27/00; C10G 69/00; C10G 2400/04; C10G 2400/30; C10G 2300/4006; C10G 65/00; C10G 45/44; C10G 65/12; C10G 33/06; C10G 45/02; C10G 35/04; F28D 7/0083; F28F 9/26; B01D 3/007; B01D 3/32; B01D 51/10; B01D 53/047; B01D 53/1462; B01D 53/185; B01D 53/343; B01D 53/48; B01D 53/8603; B01D 53/96; B01D 2252/204; F01D 17/145; H02K 7/1823; C01B 3/24; C10K 3/04; C02F 1/586; C07C 7/08; C10L 3/103; C10L 3/104; C10L 3/101
USPC ............................ 60/655, 651, 671, 676, 698
See application file for complete search history.

(56) References Cited

U.S. PATENT DOCUMENTS

| | | | |
|---|---|---|---|
| 4,109,469 A | 8/1978 | Carson | |
| 4,291,232 A | 9/1981 | Cardone | |
| 4,428,201 A | 1/1984 | Carson | |
| 4,471,619 A | 9/1984 | Nolley, Jr. | |
| 4,476,680 A | 10/1984 | Pollman | |
| 4,512,155 A | 4/1985 | Sheinbaum | |
| 4,792,390 A | 12/1988 | Staggs | |
| 5,005,360 A | 4/1991 | McMurtry | |
| 5,007,240 A | 4/1991 | Ishida | |
| 5,164,070 A * | 11/1992 | Munro | C10G 49/22 208/100 |
| 5,240,476 A * | 8/1993 | Hegarty | B01D 53/1418 60/772 |
| 5,497,624 A * | 3/1996 | Amir | F01D 15/10 60/641.2 |
| 5,562,190 A | 10/1996 | McArthur | |
| 5,667,051 A | 9/1997 | Goldberg | |
| 5,685,152 A | 11/1997 | Sterling | |
| 5,740,677 A | 4/1998 | Vestesen | |
| 5,804,060 A | 9/1998 | Benguigui et al. | |
| 6,041,849 A | 3/2000 | Karl | |
| 6,733,636 B1 | 5/2004 | Heins | |
| 7,340,899 B1 | 3/2008 | Rubak | |
| 8,046,999 B2 * | 11/2011 | Doty | F01K 3/12 60/646 |
| 8,529,202 B2 | 9/2013 | Zhang | |
| 9,328,634 B2 | 5/2016 | Ikegami | |
| 9,334,760 B2 | 5/2016 | Ernst | |
| 9,518,497 B2 | 12/2016 | Tricaud | |
| 9,562,201 B2 * | 2/2017 | Noureldin | C10J 3/84 |
| 2006/0010872 A1 | 1/2006 | Singh | |
| 2008/0128134 A1 | 6/2008 | Mudunuri | |
| 2008/0174115 A1 | 7/2008 | Lambirth | |

(56) References Cited

U.S. PATENT DOCUMENTS

| | | |
|---|---|---|
| 2008/0289588 A1 | 11/2008 | Wees et al. |
| 2008/0307789 A1 | 12/2008 | Mak |
| 2008/0314726 A1 | 12/2008 | Choros |
| 2009/0000299 A1* | 1/2009 | Ast .................... F01K 23/04 60/618 |
| 2009/0000906 A1 | 1/2009 | Petri |
| 2009/0071652 A1 | 3/2009 | Vinegar |
| 2009/0225929 A1 | 9/2009 | Genta et al. |
| 2009/0287029 A1 | 11/2009 | Anumakonda et al. |
| 2009/0301087 A1 | 12/2009 | Borissov et al. |
| 2010/0076238 A1 | 3/2010 | Brandvold |
| 2010/0146974 A1 | 6/2010 | Ast |
| 2010/0242476 A1 | 9/2010 | Ast |
| 2010/0263380 A1 | 10/2010 | Biederman |
| 2010/0319346 A1 | 12/2010 | Ast |
| 2010/0326076 A1 | 12/2010 | Ast |
| 2010/0326098 A1 | 12/2010 | Rog |
| 2011/0016863 A1 | 1/2011 | Ernst |
| 2011/0041500 A1 | 2/2011 | Riley |
| 2011/0072819 A1 | 3/2011 | Silva et al. |
| 2011/0072820 A1 | 3/2011 | Finkenrath |
| 2011/0083437 A1 | 4/2011 | Ast |
| 2011/0158858 A1 | 6/2011 | Alves |
| 2011/0203289 A1 | 8/2011 | Gutierrez |
| 2011/0314844 A1 | 12/2011 | Gu et al. |
| 2012/0000175 A1 | 1/2012 | Wormser |
| 2012/0031096 A1 | 2/2012 | Ulas Acikgoz et al. |
| 2012/0047889 A1 | 3/2012 | Ulas Acikgoz et al. |
| 2012/0085095 A1 | 4/2012 | Penton et al. |
| 2012/0085096 A1 | 4/2012 | Penton et al. |
| 2012/0085097 A1 | 4/2012 | Penton et al. |
| 2012/0087783 A1 | 4/2012 | Zhang |
| 2012/0131921 A1 | 5/2012 | Held |
| 2012/0145050 A1 | 6/2012 | Fisenko |
| 2012/0192563 A1 | 8/2012 | Kauffman |
| 2012/0198768 A1 | 8/2012 | Khosravian |
| 2012/0204817 A1 | 8/2012 | Scherffius |
| 2012/0234263 A1 | 9/2012 | Van Wees et al. |
| 2012/0279728 A1 | 11/2012 | Northrop |
| 2012/0279900 A1 | 11/2012 | Noureldin et al. |
| 2012/0285169 A1 | 11/2012 | Freund |
| 2013/0047574 A1 | 2/2013 | Kidambi |
| 2013/0062883 A1 | 3/2013 | Kaneeda |
| 2013/0090395 A1 | 4/2013 | DiGenova et al. |
| 2013/0091843 A1 | 4/2013 | Zyhowski et al. |
| 2013/0104546 A1 | 5/2013 | Goswami |
| 2013/0145763 A1 | 6/2013 | Mirmobin et al. |
| 2013/0165534 A1 | 6/2013 | McComish |
| 2013/0213040 A1 | 8/2013 | Goswami |
| 2013/0231909 A1 | 9/2013 | Noureldin |
| 2013/0238154 A1 | 9/2013 | Noureldin |
| 2013/0291808 A1 | 11/2013 | Kautto |
| 2013/0334060 A1 | 12/2013 | Koseoglu et al. |
| 2014/0090405 A1 | 4/2014 | Held et al. |
| 2014/0174084 A1 | 6/2014 | Kontomaris |
| 2014/0260311 A1 | 9/2014 | Berlowitz |
| 2014/0318124 A1 | 10/2014 | Ernst |
| 2015/0027118 A1 | 1/2015 | Tricaud |
| 2015/0073188 A1 | 3/2015 | Floudas |
| 2015/0361831 A1 | 12/2015 | Myers |
| 2015/0377079 A1 | 12/2015 | Noureldin |
| 2016/0032786 A1 | 2/2016 | Zampieri |
| 2016/0045841 A1 | 2/2016 | Kaplan |
| 2016/0076347 A1 | 3/2016 | Diez |
| 2017/0058202 A1 | 3/2017 | Noureldin |
| 2017/0058703 A1 | 3/2017 | Noureldin |
| 2017/0058704 A1 | 3/2017 | Noureldin et al. |
| 2017/0058705 A1 | 3/2017 | Noureldin |
| 2017/0058706 A1 | 3/2017 | Noureldin |
| 2017/0058708 A1 | 3/2017 | Noureldin |
| 2017/0058709 A1 | 3/2017 | Noureldin |
| 2017/0058711 A1 | 3/2017 | Noureldin |
| 2017/0058713 A1 | 3/2017 | Noureldin |
| 2017/0058714 A1 | 3/2017 | Noureldin |
| 2017/0058719 A1 | 3/2017 | Noureldin |
| 2017/0058720 A1 | 3/2017 | Noureldin |
| 2017/0058721 A1 | 3/2017 | Noureldin |
| 2017/0058722 A1 | 3/2017 | Noureldin |
| 2017/0058723 A1 | 3/2017 | Noureldin |

FOREIGN PATENT DOCUMENTS

| | | |
|---|---|---|
| CN | 104560082 | 4/2015 |
| DE | 3731978 | 3/1988 |
| EP | 0292391 | 11/1988 |
| EP | 949318 | 10/1999 |
| EP | 2516326 | 10/2012 |
| FR | 2990990 A1 | 11/2013 |
| SU | 295317 | 10/1977 |
| WO | WO 97/21786 A1 | 6/1997 |
| WO | 2004102082 | 11/2004 |
| WO | 2011090553 | 7/2011 |
| WO | WO2012048132 A2 | 4/2012 |
| WO | WO2013055864 A1 | 4/2013 |
| WO | 2014205163 | 12/2014 |

OTHER PUBLICATIONS

Bourji et al., "Optimizing an Organic Rankine Cycle," CEP—Chemical Engineering Progress, Jan. 2013, 6 pages.

Handayani et al., "Opportunities for Organic Rankine Cycles (ORCs) in the Process Industries," Newcastle University, Oct. 25-26, 2011, 40 pages.

Kapil et al., "Advanced Process Integration for Low Grade Heat Recovery," published on or before Mar. 2010, 58 pages.

Meacher, Organic Rankine Cycle Systems for Waste Heat Recovery in Refineries and Chemical Process Plants, Proceedings from the Third Industrial Energy Technology Conference Houston, TX, Apr. 26-29, 1981, 8 pages.

Rowshanaie et al., "Generating the Electricity from Fluegas Produced by Boiler through a ORC Thermodynamic Cycle (Organic Rankine Cycle) by using a Shaft Tightness in Turbo-Expander," International Conference on Chemical, Agricultural and Medical Sciences, Dec. 29-30, 2013, 4 pages.

Tillman, "Low Temperature Waste Energy Recovery in Chemical Plants and Refineries," TAS Energy Inc., May 16, 2012, 11 pages.

Bertrand F. Tchanche, Gr. Lambrinos, A. Frangoudakis and G. Papadakis "Low-grade heat conversion into power using organic Rankine cycles—A review of various applications", Renewable and Sustainable Energy Reviews, 15 (2011) 3963-3979 (abstract provided, full article can be provided upon request).

Jung et al., "Feasibility assessment of refinery waste heat to power conversion using an organic Rankine cycle", Energy conversion and Management, vol. 77, published in 2014, pp. 396-407.

Jose Maria Ponce-Ortega, et al., "Optimal design of inter-plant waste energy integration", Applied Thermal Engineering, 62 (2014), 633-652 (abstract provided, full article can be provided upon request).

Kevin J.DiGenova, Barbara B.Botros, and J.G. Brisson, "Method for customizing an organic Rankine cycle to a complex heat source for efficient energy conversion, demonstrated on a Fischer Tropsch plant", Applied energy, 102 (2013), 746-754 (abstract provided, full article can be provided upon request).

PCT International Search Report and Written Opinion of the International Searching Authority, PCT/US2016/048219, Nov. 21, 2016, 13 pages.

Hasan et al., "First and Second Law Analysis of a New Power and Refrigeration Thermodynamic Cycle using a Solar Heat Source," Pergamon, Solar Energy, vol. 73, No. 5, Nov. 1, 2002, pp. 385-393.

Stecco, "Kalina Cycles: Some Possible Applications and Comments," Proceedings of the American Power Conference, XP 000609703, Jan. 1, 1993, vol. 1, pp. 196-201.

Tamm et al., "Theoretical and Experimental Investigation of an Ammonia-Water Power and Refrigeration Thermodynamic Cycle," Science Direct, Solar Energy, vol. 76, No. 1-3, Jan. 1, 2004, pp. 217-228.

Sadrameli et al., "Optimum Operating Conditions for a Combined Power and Cooling Thermodynamic Cycle," Science Direct, Applied Energy, vol. 84, No. 3, Nov. 10, 2006, pp. 254-265.

(56) References Cited

OTHER PUBLICATIONS

Vidal, "Analysis of a Combined Power and Refrigeration Cycle by the Exergy Method," Science Direct, Energy 31, Dec. 1, 2006, pp. 3401-3414.
PCT International Search Report and Written Opinion of the International Searching Authority, PCT/US2016/027417, Jul. 6, 2016, 11 pages.
PCT International Search Report and Written Opinion of the International Searching Authority, PCT/US2016/027797, Oct. 19, 2016, 12 pages.
PCT International Search Report and Written Opinion of the International Searching Authority, PCT/US2016/027794, Oct. 19, 2016, 13 pages.
PCT International Search Report and Written Opinion of the International Searching Authority, PCT/US2016/030063, Oct. 19, 2016, 13 pages.
PCT International Search Report and Written Opinion of the International Searching Authority, PCT/US2016/030156, Oct. 19, 2016, 12 pages.
PCT International Search Report and Written Opinion of the International Searching Authority, PCT/US2016/048074, Nov. 9, 2016, 12 pages.
PCT International Search Report and Written Opinion of the International Searching Authority, PCT/US2016/048042, Nov. 9, 2016, 12 pages.
PCT International Search Report and Written Opinion of the International Searching Authority, PCT/US2016/048207, Nov. 21, 2016, 12 pages.
PCT International Search Report and Written Opinion of the International Searching Authority, PCT/US2016/048229, Nov. 21, 2016, 13 pages.
PCT International Search Report and Written Opinion of the International Searching Authority, PCT/US2016/048236, Nov. 21, 2016, 13 pages.
PCT International Search Report and Written Opinion of the International Searching Authority, PCT/US2016/048067, Nov. 15, 2016, 11 pages.
PCT International Search Report and Written Opinion of the International Searching Authority, PCT/US2016/048066, Nov. 15, 2016, 11 pages.
PCT International Search Report and Written Opinion of the International Searching Authority, PCT/US2016/048078, Nov. 15, 2016, 12 pages.
PCT International Search Report and Written Opinion of the International Searching Authority, PCT/US2016/048076, Nov. 15, 2016, 12 pages.
PCT International Search Report arid Written Opinion of the International Searching Authority, PCT/US2016/027413, Nov. 22, 2016, 11 pages.
PCT International Seach Report and Written Opinion of the International Searching Authority, PCT/US2016/048063, Nov. 23, 2016, 11 pages.
PCT International Search Report and Written Opinion of the International Searching Authority, PCT/US2016/048071, Nov. 23, 2016, 11 pages.
PCT International Search Report and Written Opinion of the International Searching Authority, PCT/US2016/048210, Dec. 22, 2016, 11 pages.
PCT International Search Report and Written Opinion of the International Searching Authority, PCT/US2016/048224, Dec. 22, 2016, 11 pages.
PCT International Seach Report and Written Opinion of the International Searching Authority, PCT/US2016/048209, Dec. 22, 2016, 11 pages.
PCT International Search Report and Written Opinion of the International Searching Authority, PCT/US2016/048237, Dec. 22, 2016, 11 pages.
PCT International Seach Report and Written Opinion of the International Searching Authority, PCT/US2016/048223, Dec. 22, 2016, 11 pages.
PCT International Search Report and Written Opinion of the International Searching Authority, PCT/US2016/048212, Dec. 22, 2016, 11 pages.

\* cited by examiner

POWER GENERATION USING INDEPENDENT TRIPLE ORGANIC RANKINE CYCLES FROM WASTE HEAT IN INTEGRATED CRUDE OIL REFINING AND AROMATICS FACILITIES

CROSS-REFERENCE TO RELATED APPLICATIONS

This application claims priority under 35 U.S.C. §119 to U.S. Provisional Patent Application Ser. No. 62/209,217, filed on Aug. 24, 2015; U.S. Provisional Patent Application Ser. No. 62/209,147, filed on Aug. 24, 2015; U.S. Provisional Patent Application Ser. No. 62/209,188, filed on Aug. 24, 2015; and U.S. Provisional Patent Application Ser. No. 62/209,223, filed on Aug. 24, 2015. The entire contents of each of the preceding applications are incorporated herein by reference in their respective entireties.

TECHNICAL FIELD

This specification relates to power generation in industrial facilities.

BACKGROUND

Petroleum refining processes are chemical engineering processes and other facilities used in petroleum refineries to transform crude oil into products, for example, liquefied petroleum gas (LPG), gasoline, kerosene, jet fuel, diesel oils, fuel oils, and other products. Petroleum refineries are large industrial complexes that involve many different processing units and auxiliary facilities, for example, utility units, storage tanks, and other auxiliary facilities. Each refinery can have its own unique arrangement and combination of refining processes determined, for example, by the refinery location, desired products, economic considerations, or other factors. The petroleum refining processes that are implemented to transform the crude oil into the products such as those listed earlier can generate heat, which may not be re-used, and byproducts, for example, greenhouse gases (GHG), which may pollute the atmosphere. It is believed that the world's environment has been negatively affected by global warming caused, in part, due to the release of GHG into the atmosphere.

SUMMARY

This specification describes technologies relating to power generation from waste energy in industrial facilities. The present disclosure includes one or more of the following units of measure with their corresponding abbreviations, as shown in Table 1:

TABLE 1

| Unit of Measure | Abbreviation |
| --- | --- |
| Degrees Celsius | ° C. |
| Megawatts | MW |
| One million | MM |
| British thermal unit | Btu |
| Hour | h |
| Pounds per square inch (pressure) | psi |
| Kilogram (mass) | Kg |
| Second | S |

The details of one or more implementations of the subject matter described in this specification are set forth in the accompanying drawings and the description later. Other features, aspects, and advantages of the subject matter will become apparent from the description, the drawings, and the claims.

DETAILED DESCRIPTION

Figure 1A:
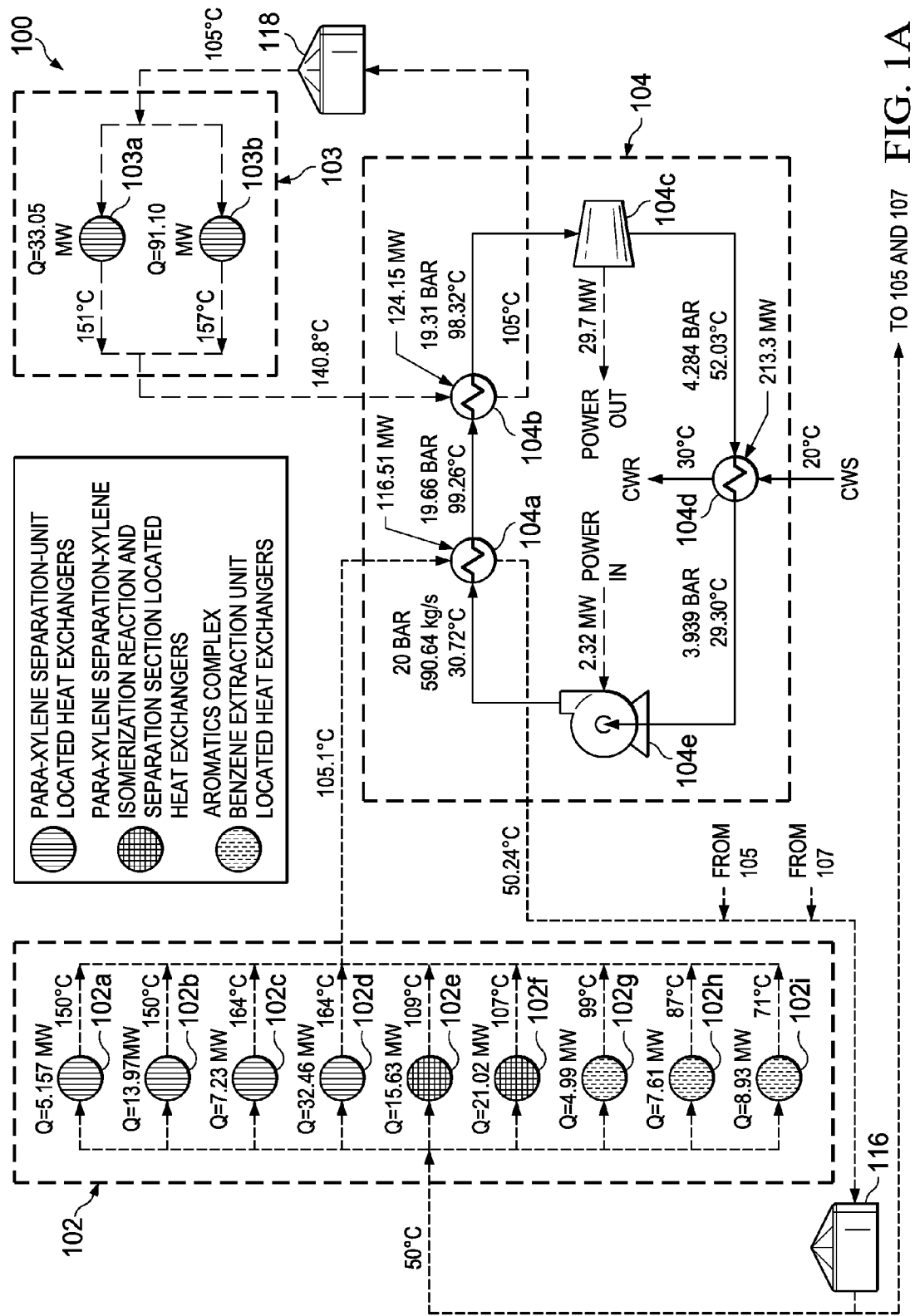
FIG. 1A is a schematic diagram of a portion of an example network to recover waste heat from eleven heat sources distributed across two heating fluid circuits.

Industrial waste heat is a source for potential carbon-free power generation in many industrial facilities, for example, crude oil refineries, petrochemical and chemical complexes, and other industrial facilities. For example, a medium-size integrated crude oil refinery with aromatics up to 4,000 MM Btu/h can be wasted to a network of air coolers extended along the crude oil and aromatics site. Some of the wasted heat can be used to power an Organic Rankine Cycle (ORC) machine, which uses an organic fluid such as refrigerants or hydrocarbons (or both) instead of water to generate power. ORC machines in combination with low temperature heat sources (for example, about or less than 232° C.) are being implemented as power generation systems. Optimizing ORC machines, for example, by optimizing the power generation cycle (that is, the Rankine cycle) or the organic fluid implemented by the ORC machine (or both), can improve power generation from recovered waste heat.

An industrial facility such as a petroleum refinery includes several sources of waste heat. One or more ORC machines can receive the waste heat from one or more or all of such sources. In some implementations, two or more sources of low grade heat can be consolidated by transferring heat from each of the sources to a common intermediate heat transfer medium (for example, water or other fluid). The intermediate heat transfer medium can then be used to evaporate the working fluid of the ORC machine to generate power, for example, to operate a turbine or other power generator. Such consolidation of sources of low grade heat can allow the ORC machine to be sized to realize greater efficiencies and economies of scale. Further, such a consolidated operation can improve flexibility in petroleum refinery design and plot space planning, since each heat source need not be in close proximity to the power generator. The proposed consolidation of heat sources, particularly, in mega sites such as a site-wide oil refinery that includes an aromatics complex and is the size of an eco-industrial park can represent an over-simplification of the problem of improving the process of recovering waste heat to generate power.

This disclosure describes optimizing power generation from waste heat, for example, low grade heat at a temperature at or less than 160° C., in large industrial facilities (for example, petroleum refineries or other large industrial refineries with several, sometimes more than 50, hot source streams) by utilizing a subset of all available hot source streams selected based, in part, on considerations for example, capital cost, ease of operation, economics of scale power generation, a number of ORC machines to be operated, operating conditions of each ORC machine, combinations of them, or other considerations. Recognizing that several subsets of hot sources can be identified from among the available hot sources in a large petroleum refinery, this disclosure describes selecting subsets of hot sources that are optimized to provide waste heat to one or more ORC machines for power generation. Further, recognizing that the utilization of waste heat from all available hot sources in a mega-site such as a petroleum refinery and aromatics complex is not necessarily or not always the best option, this disclosure identifies hot source units in petroleum refineries from which waste heat can be consolidated to power the one or more ORC machines.

This disclosure also describes modifying medium grade crude oil refining semi-conversion facilities and integrated medium grade crude oil refining semi-conversion and aromatics facilities plants' designs to improve their energy efficiencies relative to their current designs. To do so, new facilities can be designed or existing facilities can be re-designed (for example, retro-fitted with equipment) to recover waste heat, for example, low grade waste heat, from heat sources to power ORC machines. In particular, the existing design of a plant need not be significantly altered to accommodate the power generation techniques described here. The generated power can be used, in part, to power the facilities or transported to the electricity grid to be delivered elsewhere (or both).

By recovering all or part of the waste heat generated by one or more processes or facilities (or both) of industrial facilities and converting the recovered waste heat into power, carbon-free power (for example, in the form of electricity) can be generated for use by the community. The minimum approach temperature used in the waste heat recovery processes can be as small as 3° C. and the generated power can be as great as 80 MW. In some implementations, higher minimum approach temperatures can be used in an initial phase at the expense of less waste heat/energy recovery, while relatively better power generation (for example, in terms of economy of scale design and efficiency) is realized in a subsequent phase upon using the minimum approach temperature for the specific hot sources uses. In such situations, more power generation can be realized in the subsequent phase without needing to change the design topology of the initial phase or the subset of the low grade waste hot sources used in the initial phase (or both).

Not only pollution associated but also cost associated with power generation can be decreased. In addition, recovering waste heat from a customized group of hot sources to power one or more ORC machines is more optimal than recovering waste heat from all available hot sources. Selecting the hot sources in the customized group instead of or in addition to optimizing the ORC machine can improve or optimize (or both) the process of generating power from recovered waste heat. If a few number of hot sources are used for power generation, then the hot sources can be consolidated into few (for example, one or two) buffer streams using fluids, for example, hot oil or high pressure hot water system, or a mixture of the two.

In sum, this disclosure describes several petroleum refinery-wide separation/distillation networks, configurations, and processing schemes for efficient power generation using a basic ORC machine operating under specified conditions. The power generation is facilitated by obtaining all or part of waste heat, for example, low grade waste heat, carried by multiple, scattered low grade energy quality process streams. In some implementations, the ORC machine uses separate organic material to pre-heat the exchanger and evaporator and uses other organic fluid, for example, isobutane, at specific operating conditions.

Examples of Petroleum Refinery Plants

Industrial waste heat is a source for potential carbon-free power generation in many industrial facilities, for example, crude oil refineries, petrochemical and chemical complexes, and other industrial facilities. For example, a medium-size integrated crude oil refinery with aromatics up to 4,000 MM Btu/h can be wasted to a network of air coolers extended along the crude oil and aromatics site. Some of the wasted heat can be used to power an Organic Rankine Cycle (ORC) machine, which uses an organic fluid such as refrigerants or hydrocarbons (or both) instead of water to generate power. ORC machines in combination with low temperature heat sources (for example, about or less than 232° C.) are being implemented as power generation systems. Optimizing ORC machines, for example, by optimizing the power generation cycle (that is, the Rankine cycle) or the organic fluid implemented by the ORC machine (or both), can improve power generation from recovered waste heat.

An industrial facility such as a petroleum refinery includes several sources of waste heat. One or more ORC machines can receive the waste heat from one or more or all of such sources. In some implementations, two or more sources of low grade heat can be consolidated by transferring heat from each of the sources to a common intermediate heat transfer medium (for example, water or other fluid). The intermediate heat transfer medium can then be used to evaporate the working fluid of the ORC machine to generate power, for example, to operate a turbine or other power generator. Such consolidation of sources of low grade heat can allow the ORC machine to be sized to realize greater efficiencies and economies of scale. Further, such a consolidated operation can improve flexibility in petroleum refinery design and plot space planning, since each heat source need not be in close proximity to the power generator. The proposed consolidation of heat sources, particularly, in mega sites such as a site-wide oil refinery that includes an aromatics complex and is the size of an eco-industrial park can represent an over-simplification of the problem of improving the process of recovering waste heat to generate power.

This disclosure describes optimizing power generation from waste heat, for example, low grade heat at a temperature at or less than 160° C., in large industrial facilities (for example, petroleum refineries or other large industrial refineries with several, sometimes more than 50, hot source streams) by utilizing a subset of all available hot source streams selected based, in part, on considerations for example, capital cost, ease of operation, economics of scale power generation, a number of ORC machines to be operated, operating conditions of each ORC machine, combinations of them, or other considerations. Recognizing that several subsets of hot sources can be identified from among the available hot sources in a large petroleum refinery, this disclosure describes selecting subsets of hot sources that are optimized to provide waste heat to one or more ORC machines for power generation. Further, recognizing that the utilization of waste heat from all available hot sources in a mega-site such as a petroleum refinery and aromatics complex is not necessarily or not always the best option, this disclosure identifies hot source units in petroleum refineries from which waste heat can be consolidated to power the one or more ORC machines.

This disclosure also describes modifying medium grade crude oil refining semi-conversion facilities and integrated medium grade crude oil refining semi-conversion and aromatics facilities plants' designs to improve their energy efficiencies relative to their current designs. To do so, new facilities can be designed or existing facilities can be re-designed (for example, retro-fitted with equipment) to recover waste heat, for example, low grade waste heat, from heat sources to power ORC machines. In particular, the existing design of a plant need not be significantly altered to accommodate the power generation techniques described here. The generated power can be used, in part, to power the facilities or transported to the electricity grid to be delivered elsewhere (or both).

By recovering all or part of the waste heat generated by one or more processes or facilities of industrial facilities (or both) and converting the recovered waste heat into power, carbon-free power (for example, in the form of electricity) can be generated for use by the community. The minimum approach temperature used in the waste heat recovery processes can be as small as 3° C. and the generated power can be as great as 80 MW. In some implementations, higher minimum approach temperatures can be used in an initial phase at the expense of less waste heat/energy recovery, while relatively better power generation (for example, in terms of economy of scale design and efficiency) is realized in a subsequent phase upon using the minimum approach temperature for the specific hot sources uses. In such situations, more power generation can be realized in the subsequent phase without needing to change the design topology of the initial phase or the subset of the low grade waste hot sources used in the initial phase (or both).

Not only pollution associated but also cost associated with power generation can be decreased. In addition, recovering waste heat from a customized group of hot sources to power one or more ORC machines is more cost effective from a capital cost point-of-view than recovering waste heat from all available hot sources. Selecting the hot sources in the customized group instead of or in addition to optimizing the ORC machine can improve or optimize the process of generating power from recovered waste heat (or both). If a few number of hot sources are used for power generation, then the hot sources can be consolidated into few (for example, one or two) buffer streams using fluids, for example, hot oil or high pressure hot water system (or both).

In sum, this disclosure describes several petroleum refinery-wide separation/distillation networks, configurations, and processing schemes for efficient power generation using a basic ORC machine operating under specified conditions. The power generation is facilitated by obtaining all or part of waste heat, for example, low grade waste heat, carried by multiple, scattered low grade energy quality process streams. In some implementations, the ORC machine uses separate organic material to pre-heat the exchanger and evaporator and uses other organic fluid, for example, isobutane, at specific operating conditions.

Examples of Petroleum Refinery Plants

1. Hydrocracking Plant

Hydrocracking is a two-stage process combining catalytic cracking and hydrogenation. In this process heavy feedstocks are cracked in the presence of hydrogen to produce more desirable products. The process employs pressure, temperature, a catalyst, and hydrogen. Hydrocracking is used for feedstocks that are difficult to process by either catalytic cracking or reforming, since these feedstocks are characterized usually by high polycyclic aromatic content or high concentrations of the two principal catalyst poisons, sulfur and nitrogen compounds (or both).

The hydrocracking process depends on the nature of the feedstock and the relative rates of the two competing reactions, hydrogenation and cracking. Heavy aromatic feedstock is converted into lighter products under a wide range of high pressures and high temperatures in the presence of hydrogen and special catalysts. When the feedstock has paraffinic content, hydrogen prevents the formation of polycyclic aromatic compounds. Hydrogen also reduces tar formation and prevents buildup of coke on the catalyst. Hydrogenation additionally converts sulfur and nitrogen compounds present in the feedstock to hydrogen sulfide and ammonia. Hydrocracking produces isobutane for alkylation feedstock, and also performs isomerization for pour-point control and smoke-point control, both of which are important in high-quality jet fuel.

2. Diesel Hydrotreating Plant

Hydrotreating is a refinery process for reducing sulfur, nitrogen and aromatics while enhancing cetane number, density and smoke point. Hydrotreating assists the refining industry's efforts to meet the global trend for stringent clean fuels specifications, the growing demand for transportation fuels and the shift toward diesel. In this process, fresh feed is heated and mixed with hydrogen. Reactor effluent exchanges heat with the combined feed and heats recycle gas and stripper charge. Sulphide (for example, ammonium bisulphide and hydrogen sulphide) is then removed from the feed.

3. Aromatics Complex

A typical aromatics complex includes a combination of process units for the production of basic petrochemical intermediates of benzene, toluene and xylenes (BTX) using the catalytic reforming of naphtha using continuous catalyst regeneration (CCR) technology.

4. Naphtha Hydrotreating Plant and Continuous Catalytic Reformer Plants

A Naphtha Hydrotreater (NHT) produces 101 Research Octane Number (RON) reformate, with a maximum 4.0 psi Reid Vapor Pressure (RVP), as a blending stock in the gasoline pool. It usually has the flexibility to process blends of Naphtha from the Crude Unit, Gas Condensate Splitter, Hydrocracker, Light Straight-Run Naphtha (LSRN) and Visbreaker Plants. The NHT processes naphtha to produce desulfurized feed for the continuous catalyst regeneration (CCR) platformer and gasoline blending.

5. Crude Distillation Plant

Normally, a two-stage distillation plant processes various crude oils that are fractionated into different products, which are further processed in downstream facilities to produce liquefied petroleum gas (LPG), Naphtha, Motor Gasoline, Kerosene, Jet Fuel, Diesel, Fuel Oil and Asphalt. The Crude Distillation plant can typically process large volumes, for example, hundreds of thousands of barrels, of crude oil per day. During the summer months the optimum processing capacity may decrease. The plant can process mixture of crudes. The plant can also have asphalt producing facilities. The products from crude distillation plant are LPG, stabilized whole naphtha, kerosene, diesel, heavy diesel, and vacuum residuum. The Atmospheric Column receives the crude charge and separates it into overhead product, kerosene, diesel, and reduced crude. The Naphtha stabilizer may receive the atmospheric overhead stream and separates it into LPG and stabilized naphtha. The reduced crude is charged to the Vacuum tower where it is further separated into heavy diesel, vacuum gas oils and vacuum residuum.

6. Sour Water Stripping Utility Plant (SWSUP)

The SWSUP receives sour water streams from acid gas removal, sulfur recovery, and flare units, and the sour gas stripped and released from the soot water flash vessel. The SWSUP strips the sour components, primarily carbon dioxide ($CO_2$), hydrogen sulfide ($H_2S$) and ammonia ($NH_3$), from the sour water stream.

One of more of the refinery plants described earlier can supply heat, for example, in the form of low grade waste heat, to the ORC machine with reasonable economics of scale, for example, tens of megawatts of power. Studies have shown that particular refinery plants, for example, a hydrocracking plant, serve as good waste heat sources to generate power. However, in a study using only the hot source from the naphtha hydrotreating (NHT) plant, for example, at about 111° C., 1.7 MW of power was produced from about 27.6 MW of available waste heat at a low efficiency of about 6.2%. The low efficiency suggests that a hot source from the NHT plant alone is not recommended for waste heat generation due to high capital and economy of scale. In another study using one low grade hot source at about 97° C. from a crude distillation plant, 3.5 MW of power was produced from about 64.4 MW of available waste heat at a low efficiency of 5.3%. In a further study using one low grade hot source at about 120° C. from a sour water stripping plant, 2.2 MW of power was produced from about 32.7 MW of available waste heat at a low efficiency of 6.7%. These studies reveal that if waste heat recovery from a particular refinery plant to generate power is determined to be beneficial, it does not necessarily follow that waste heat recovery from any refinery plant will also be beneficial.

In another study, all waste heat available from all hot sources (totaling 11 hot source streams) in an aromatics complex were collected to generate about 13 MW of power from about 241 MW of available waste heat. This study reveals that using all available hot sources, while theoretically efficient, does not, in practice, necessarily translate to efficient power generation from available waste heat. Moreover, assembling power plants that can use all available hot sources can be very difficult considering the quantity of heat exchangers, pumps, and organic-based turbines (among other components and inter-connectors) involved. Not only will it be difficult to retrofit existing refineries to accommodate such power plants, but it will also be difficult to build such power plants from a grass roots stage. In the following sections, this disclosure describes combinations of hot sources selected from different refinery plants which can result in high efficiencies in generating power from available waste heat.

Even after identifying specific hot sources to be used for power generation in a mega-size site, there can be several combinations of hot sources that can be integrated for optimum generation of power using a specific ORC machine operating under specific conditions. Each of the following sections describes a specific combination of hot sources and a configuration for buffer systems which can be implemented with the specific combination to optimally generate power from waste heat with as minimum capital utilization as necessary. Also, the following sections describe two-buffer systems for low grade waste heat recovery where one-buffer systems for waste heat recovery as inapplicable. Each section describes the interconnections and related processing schemes between the different plants that make up the specific combination of hot sources, the configurations including components such as heat exchangers added in specific plants, at specific places and to specific streams in the process to optimize waste heat recovery and power generation. As described later, the different configurations can be implemented without changing the current layout or processes implemented by the different plants. The new configurations described in the sections later can generate between about 34 MW and about 80 MW of power from waste heat, enabling a proportional decrease of GHG emissions in petroleum refineries. The configurations described in the sections later demonstrate more than one way to achieve desired energy recovery using buffer systems. The configurations are related processing schemes do not impact and can be integrated with future potential in-plant energy saving initiatives, for example, low pressure steam generation. The configurations and processing schemes can render more than 10% first law efficiency for power generation from the low grade waste heat into the ORC machine.

Heat Exchangers

In the configurations described in this disclosure, heat exchangers are used to transfer heat from one medium (for example, a stream flowing through a plant in a crude oil refining facility, a buffer fluid or other medium) to another medium (for example, a buffer fluid or different stream flowing through a plant in the crude oil facility). Heat exchangers are devices which transfer (exchange) heat typically from a hotter fluid stream to a relatively cooler fluid stream. Heat exchangers can be used in heating and cooling applications, for example, in refrigerators, air conditions or other cooling applications. Heat exchangers can be distinguished from one another based on the direction in which liquids flow. For example, heat exchangers can be parallel-flow, cross-flow or counter-current. In parallel-flow heat exchangers, both fluid involved move in the same direction, entering and exiting the heat exchanger side-by-side. In cross-flow heat exchangers, the fluid path runs perpendicular to one another. In counter-current heat exchangers, the fluid paths flow in opposite directions, with one fluid exiting whether the other fluid enters. Counter-current heat exchangers are sometimes more effective than the other types of heat exchangers.

In addition to classifying heat exchangers based on fluid direction, heat exchangers can also be classified based on their construction. Some heat exchangers are constructed of multiple tubes. Some heat exchangers include plates with room for fluid to flow in between. Some heat exchangers enable heat exchange from liquid to liquid, while some heat exchangers enable heat exchange using other media.

Heat exchangers in crude oil refining and petrochemical facilities are often shell and tube type heat exchangers which include multiple tubes through which liquid flows. The tubes are divided into two sets—the first set contains the liquid to be heated or cooled; the second set contains the liquid responsible for triggering the heat exchange, in other words, the fluid that either removes heat from the first set of tubes by absorbing and transmitting the heat away or warms the first set by transmitting its own heat to the liquid inside. When designing this type of exchanger, care must be taken in determining the correct tube wall thickness as well as tube diameter, to allow optimum heat exchange. In terms of flow, shell and tube heat exchangers can assume any of three flow path patterns.

Heat exchangers in crude oil refining and petrochemical facilities can also be plate and frame type heat exchangers. Plate heat exchangers include thin plates joined together with a small amount of space in between, often maintained by a rubber gasket. The surface area is large, and the corners of each rectangular plate feature an opening through which fluid can flow between plates, extracting heat from the plates as it flows. The fluid channels themselves alternate hot and cold liquids, meaning that the heat exchangers can effectively cool as well as heat fluid. Because plate heat exchangers have large surface area, they can sometimes be more effective than shell and tube heat exchangers.

Other types of heat exchangers can include regenerative heat exchangers and adiabatic wheel heat exchangers. In a regenerative heat exchanger, the same fluid is passed along both sides of the exchanger, which can be either a plate heat exchanger or a shell and tube heat exchanger. Because the fluid can get very hot, the exiting fluid is used to warm the incoming fluid, maintaining a near constant temperature. Energy is saved in a regenerative heat exchanger because the process is cyclical, with almost all relative heat being transferred from the exiting fluid to the incoming fluid. To maintain a constant temperature, a small quantity of extra energy is needed to raise and lower the overall fluid temperature. In the adiabatic wheel heat exchanger, an intermediate liquid is used to store heat, which is then transferred to the opposite side of the heat exchanger. An adiabatic wheel consists of a large wheel with treads that rotate through the liquids—both hot and cold—to extract or transfer heat. The heat exchangers described in this disclosure can include any one of the heat exchangers described earlier, other heat exchangers, or combinations of them.

Each heat exchanger in each configuration can be associated with a respective thermal duty (or heat duty). The thermal duty of a heat exchanger can be defined as an amount of heat that can be transferred by the heat exchanger from the hot stream to the cold stream. The amount of heat can be calculated from the conditions and thermal properties of both the hot and cold streams. From the hot stream point of view, the thermal duty of the heat exchanger is the product of the hot stream flow rate, the hot stream specific heat, and a difference in temperature between the hot stream inlet temperature to the heat exchanger and the hot stream outlet temperature from the heat exchanger. From the cold stream point of view, the thermal duty of the heat exchanger is the product of the cold stream flow rate, the cold stream specific heat and a difference in temperature between the cold stream outlet from the heat exchanger and the cold stream inlet temperature from the heat exchanger. In several applications, the two quantities can be considered equal assuming no heat loss to the environment for these units, particularly, where the units are well insulated. The thermal duty of a heat exchanger can be measured in watts (W), megawatts (MW), millions of British Thermal Units per hour (Btu/hr), or millions of kilocalories per hour (Kcal/h). In the configurations described here, the thermal duties of the heat exchangers are provided as being "about X MW," where "X" represents a numerical thermal duty value. The numerical thermal duty value is not absolute. That is, the actual thermal duty of a heat exchanger can be approximately equal to X, greater than X or less than X.

Flow Control System

In each of the configurations described later, process streams (also called "streams") are flowed within each plant in a crude oil refining facility and between plants in the crude oil refining facility. The process streams can be flowed using one or more flow control systems implemented throughout the crude oil refining facility. A flow control system can include one or more flow pumps to pump the process streams, one or more flow pipes through which the process streams are flowed and one or more valves to regulate the flow of streams through the pipes.

In some implementations, a flow control system can be operated manually. For example, an operator can set a flow rate for each pump and set valve open or close positions to regulate the flow of the process streams through the pipes in the flow control system. Once the operator has set the flow rates and the valve open or close positions for all flow control systems distributed across the crude oil refining facility, the flow control system can flow the streams within a plant or between plants under constant flow conditions, for example, constant volumetric rate or other flow conditions. To change the flow conditions, the operator can manually operate the flow control system, for example, by changing the pump flow rate or the valve open or close position.

In some implementations, a flow control system can be operated automatically. For example, the flow control system can be connected to a computer system to operate the flow control system. The computer system can include a computer-readable medium storing instructions (such as flow control instructions and other instructions) executable by one or more processors to perform operations (such as flow control operations). An operator can set the flow rates and the valve open or close positions for all flow control systems distributed across the crude oil refining facility using the computer system. In such implementations, the operator can manually change the flow conditions by providing inputs through the computer system. Also, in such implementations, the computer system can automatically (that is, without manual intervention) control one or more of the flow control systems, for example, using feedback systems implemented in one or more plants and connected to the computer system. For example, a sensor (such as a pressure sensor, temperature sensor or other sensor) can be connected to a pipe through which a process stream flows. The sensor can monitor and provide a flow condition (such as a pressure, temperature, or other flow condition) of the process stream to the computer system. In response to the flow condition exceeding a threshold (such as a threshold pressure value, a threshold temperature value, or other threshold value), the computer system can automatically perform operations. For example, if the pressure or temperature in the pipe exceeds the threshold pressure value or the threshold temperature value, respectively, the computer system can provide a signal to the pump to decrease a flow rate, a signal to open a valve to relieve the pressure, a signal to shut down process stream flow, or other signals.

This disclosure describes a waste heat recovery network that can be implemented to recover heat from a diesel hydro-treating plant sub-unit, a hydrocracking plant sub-unit and an aromatics plant sub-unit of a petrochemical refining system. As described later, heat recovered from the waste heat recovery network can be used to generate about 75 MW of power, thereby increasing a heat generation efficiency of the petrochemical refining system by about 12.3%. The waste heat recovery network described here can be implemented either in its entirety or in phases. Each phase can be separately implemented without hindering previously implemented phases or future phases. The minimum approach temperature used in the waste heat recovery network described here can be as small as 3° C. Alternatively, higher minimum approach temperatures can be used in the beginning to achieve lower waste heat recovery. By decreasing the minimum approach temperature over time, reasonable power generation economies of scale can be used and higher power generation efficiency can be realized. Efficiency can also be increased by using a sub-set of the waste heat streams that are used in the network. The waste heat recovery network can be retrofitted to an existing petrochemical refining system layout, thereby decreasing a quantity of work needed to change the existing design topology of the petrochemical refining system.

The waste heat recovery network includes four heating fluid circuits, each thermally coupled to multiple heat sources from multiple sub-units of the petrochemical refining system. The multiple sub-units include a diesel hydro-treating plant, a hydrocracking plant and an aromatics plant. The aromatics plant can include separation sections, for example, Para-Xylene separation sections, Xylene Isomerization sections, or other separation sections. The heat recovered using the waste heat recovery network can be provided to three power generation systems. Each power generation system comprises an Organic Rankine Cycle (ORC). A first power generation system can generate about 30 MW of power. A second power generation system can generate about 32 MW of power. A third power generation system can generate about 13 MW of power. The design configuration of the waste heat recovery network and the processes implemented using the waste heat recovery network need not change with future efforts inside individual plants to enhance energy efficiency. The design configuration and the processes also need not be changed in response to other improvements to waste heat recovery in the petrochemical refining system.

Figure 1B:
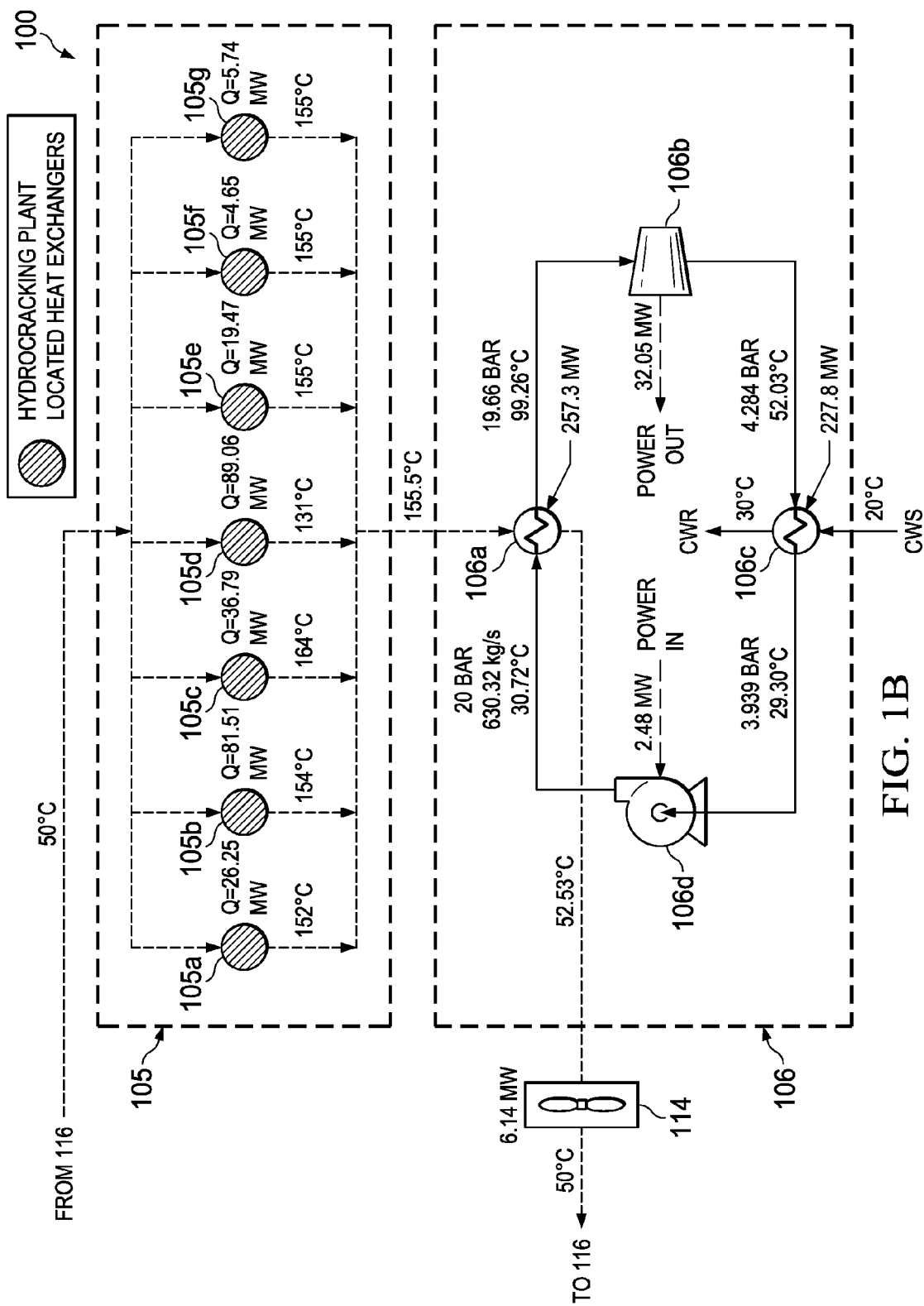
FIG. 1B is a schematic diagram of a portion of the example network to recover waste heat from seven heat sources in a heating fluid circuit.
Figure 1C:
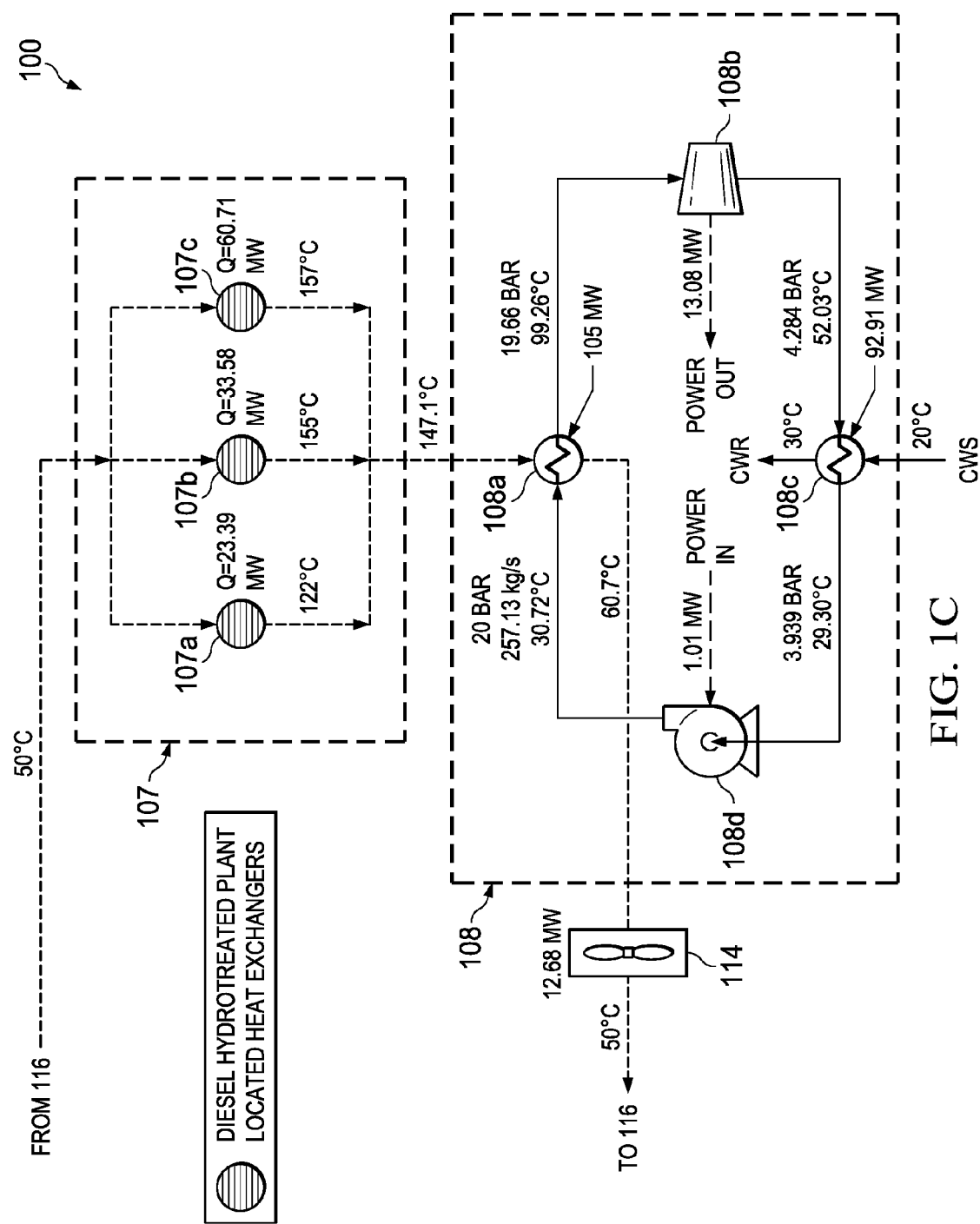
FIG. 1C is a schematic diagram of a portion of the example network to recover waste heat from three heat sources in a heating fluid circuit.

FIG. 1A is a schematic diagram of a portion of an example network to recover waste heat from eleven heat sources distributed across two heating fluid circuits. FIG. 1B is a schematic diagram of a portion of the example network to recover waste heat from seven heat sources in a heating fluid circuit. FIG. 1C is a schematic diagram of a portion of the example network to recover waste heat from three heat sources in a heating fluid circuit. FIGS. 1D-1M are schematic diagrams of heat sources in an aromatics plant. FIGS. 1N-1P are schematic diagrams of heat sources in a hydrocracking plant. FIGS. 1Q and 1R are schematic diagrams of heat sources in a diesel hydro-treating plant.

FIG. 1A is a schematic diagram of a portion of an example network 100 to recover waste heat from eleven heat sources distributed across two heating fluid circuits. In some implementations, the network can include a first heating fluid circuit 102 coupled to multiple heat sources. For example, the multiple heat sources can include nine heat exchangers (a first heat exchanger 102a, a second heat exchanger 102b, a third heat exchanger 102c, a fourth heat exchanger 102d, a fifth heat exchanger 102e, a sixth heat exchanger 102f, a seventh heat exchanger 102g, an eighth heat exchanger 102h, and a ninth heat exchanger 102i). All the heat exchangers in the first heating fluid circuit 102 can be coupled to an aromatics plant, specifically, to one of an extract column, a purification column overhead section, a Raffinate column overhead section, a heavy reformate splitter, a para-Xylene reaction section or a de-heptanizer of the aromatics plant. The nine heat sources in the first heating fluid circuit 102 can be connected in parallel.

The network can include a second heating fluid circuit 103 coupled to multiple heat sources. For example, the multiple heat sources can include two heat exchangers (a first heat exchanger 103a and a second heat exchanger 103b). Both the heat exchangers in the second heating fluid circuit 103 can be coupled to the aromatics plant. Both heat sources in the second heating fluid circuit 103 can be connected in parallel.

The portion of the example network can include a first power generation system 104 that includes an organic Rankine cycle (ORC). The ORC can include a working fluid that is thermally coupled to the first heating fluid circuit 102 and the second heating fluid circuit 103 to heat the working fluid. In some implementations, the working fluid can be isobutane. The ORC can include a gas expander 104c configured to generate electrical power from the heated working fluid. As shown in FIG. 1A, the ORC can additionally include an evaporator 104b, a pump 104e, a condenser 104d and a pre-heater 104a. In some implementations, the working fluid can be thermally coupled to 103 the first heating fluid circuit 102 in the pre-heater 104a, and to the second heating fluid in the evaporator 104b.

FIG. 1B is a schematic diagram of a portion of the example network 100 to recover waste heat from seven heat sources. In some implementations, the network can include a third heating fluid circuit 105 coupled to multiple heat sources. For example, the multiple heat sources can include seven heat exchangers (a first heat exchanger 105a, a second heat exchanger 105b, a third heat exchanger 105c, a fourth heat exchanger 105d, a fifth heat exchanger 105e, a sixth heat exchanger 105f, and a seventh heat exchanger 105g). All the heat exchangers in the third heating fluid circuit 105 can be coupled to a hydrocracking plant. The seven heat sources in the third heating fluid circuit 105 can be connected in parallel.

The portion of the example network can include a second power generation system 106 that includes an organic Rankine cycle (ORC). The ORC can include a working fluid that is thermally coupled to the third heating fluid circuit 105 to heat the working fluid. In some implementations, the working fluid can be isobutane. The ORC can include a gas expander 106b configured to generate electrical power from the heated working fluid. As shown in FIG. 1B, the ORC can additionally include an evaporator 106a, a pump 106d and a condenser 106c. In some implementations, the working fluid can be thermally coupled to the third heating fluid circuit 105 in the evaporator 106a. As further shown in FIG. 1B, an air cooler 114 cools the heat recovery circuit 105 exiting the evaporator 106a before the heating fluid in the circuit 105 is circulated to the heating fluid tank 116.

FIG. 1C is a schematic diagram of a portion of the example network 100 to recover waste heat from three heat sources. In some implementations, the network can include a fourth heating fluid circuit 107 coupled to multiple heat sources. For example, the multiple heat sources can include three heat exchangers (a first heat exchanger 107a, a second heat exchanger 107b and a third heat exchanger 107c). All the heat exchangers in the fourth heating fluid circuit 107 can be coupled to a diesel hydro-treating plant. The three heat sources in the fourth heating fluid circuit 107 can be connected in parallel.

The portion of the example network can include a third power generation system 108 that includes an organic Rankine cycle (ORC). The ORC can include a working fluid that is thermally coupled to the fourth heating fluid circuit 107 to heat the working fluid. In some implementations, the working fluid can be isobutane. The ORC can include a gas expander 108b configured to generate electrical power from the heated working fluid. As shown in FIG. 1C, the ORC can additionally include an evaporator 108a, a pump 108d and a condenser 108c. In some implementations, the working fluid can be thermally coupled to the fourth heating fluid circuit 107 in the evaporator 108a. As further shown in FIG. 1C, an air cooler 114 cools the heat recovery circuit 107 exiting the evaporator 108a before the heating fluid in the circuit 107 is circulated to the heating fluid tank 116.

In operation, a heating fluid (for example, water, oil, or other fluid) is circulated through each heating fluid circuit. For example, a portion of the heating fluid is circulated through the nine heat exchangers in the first heating fluid circuit 102. An inlet temperature of the heating fluid that is circulated into the inlets of each of the nine heat sources in the first heating fluid circuit 102 is the same or substantially the same subject to any temperature variations that may result as the heating fluid flows through respective inlets. Each heat exchanger in the first heating fluid circuit 102 heats the heating fluid to a temperature that is greater than the inlet temperature. The heated heating fluids from the nine heat exchangers in the first heating fluid circuit 102 are combined and flowed through the pre-heater 104a of the ORC of the first power generation system 104. The heating fluid flowed through the pre-heater 104a is then collected in a heating fluid tank 116 and can be pumped back through the nine heat exchangers in the first heating fluid circuit 102 to restart the waste heat recovery cycle using the first heating fluid circuit 102.

Similarly, for example, a portion of the heating fluid is circulated through the two heat exchangers in the second heating fluid circuit 103. An inlet temperature of the heating fluid that is circulated into the inlets of each of the heat sources in the second heating fluid circuit 103 is the same or substantially the same subject to any temperature variations that may result as the heating fluid flows through respective inlets. Each heat exchanger in the second heating fluid circuit 103 heats the heating fluid to a temperature that is greater than the inlet temperature. The heated heating fluids from both heat exchangers in the second heating fluid circuit 103 are combined and flowed through the evaporator 104b of the ORC of the first power generation system 104. The heating fluid flowed through the evaporator 104b is then collected in a heating fluid tank 118 and can be pumped back through the two heat exchangers in the second heating fluid circuit 103 to restart the waste heat recovery cycle using the second heating fluid circuit 103.

Similarly, for example, a portion of the heating fluid is circulated through the seven heat exchangers in the third heating fluid circuit 105. An inlet temperature of the heating fluid that is circulated into the inlets of each of the heat sources in the third heating fluid circuit 105 is the same or substantially the same subject to any temperature variations that may result as the heating fluid flows through respective inlets. Each heat exchanger in the third heating fluid circuit 105 heats the heating fluid to a temperature that is greater than the inlet temperature. The heated heating fluids from the seven heat exchangers in the third heating fluid circuit 105 are combined and flowed through the evaporator 106a of the ORC of the second power generation system 106. The heating fluid flowed through the evaporator 106a is then collected in the heating fluid tank 116 and can be pumped back through the seven heat exchangers in the third heating fluid circuit 105 to restart the waste heat recovery cycle using the third heating fluid circuit 105.

Similarly, for example, a portion of the heating fluid is circulated through the three heat exchangers in the fourth heating fluid circuit 107. An inlet temperature of the heating fluid that is circulated into the inlets of each of the heat sources in the fourth heating fluid circuit 107 is the same or substantially the same subject to any temperature variations that may result as the heating fluid flows through respective inlets. Each heat exchanger in the fourth heating fluid circuit 107 heats the heating fluid to a temperature that is greater than the inlet temperature. The heated heating fluids from the three heat exchangers in the fourth heating fluid circuit 107 are combined and flowed through the evaporator 108a of the ORC of the third power generation system 108. The heating fluid flowed through the evaporator 108a is then collected in the heating fluid tank 116 and can be pumped back through the three heat exchangers in the fourth heating fluid circuit 107 to restart the waste heat recovery cycle using the fourth heating fluid circuit 107.

In the manner described earlier, the heating fluid can be looped through the 21 heat exchangers distributed across the four heating fluid circuits to recover heat that would otherwise go to waste in the diesel hydro-treating plant, the hydrocracking plant and the aromatics plant, and to use the recovered waste heat to operate three power generation systems. By doing so, an amount of energy needed to operate the three power generation systems can be decreased while obtaining the same or substantially similar power output from the three power generation systems. For example, the power output from the power generation system that implements the waste heat recovery network can be higher or lower than the power output from the power generation system that does not implement the waste heat recovery network. Where the power output is less, the difference may not be statistically significant. Consequently, a power generation efficiency of the petrochemical refining system can be increased.

The heating fluids received from the nine heat exchangers in the first heating circuit are mixed in the main header resulting in a heating fluid at a temperature of about 105° C. The heated heating fluid from the first heating fluid circuit 102 is circulated through the pre-heater 104a of the ORC of the first power generation system 104. The heating fluids received from the two heat exchangers in the second heating circuit are mixed in the main header resulting in a heating fluid at a temperature of about 141° C. The heated heating fluid from the second heating fluid circuit 103 is circulated through the evaporator 104b of the ORC of the first power generation system 104. In some implementations, the pre-heater 104a and the evaporator 104b increase the temperature of the working fluid (for example, isobutane or other working fluid) from about 31° C. at about 20 bar to about 98° C. at about 20 bar at a thermal duty of about 117 MW and 124 MW, respectively. The gas expander 104c expands the high temperature, high pressure working fluid to generate power, for example, about 30 MW, at an efficiency of about 85%. The expansion decreases the temperature and pressure of the working fluid, for example, to about 52° C. and about 4.3 bar, respectively. The working fluid flows through the condenser 104d which further decreases the temperature and pressure of the working fluid at a thermal duty of about 213 MW. For example, cooling fluid flows through the condenser 104d at a lower temperature, for example, about 20° C., exchanges heat with the working fluid, and exits the condenser 104d at a higher temperature, for example, about 30° C. The cooled working fluid (for example, isobutane liquid) is pumped by the pump 104e at an efficiency, for example, of about 75%, and an input power, for example, of about 2 MW. The pump 104e increases the temperature of the working fluid to about 31° C. and pumps the working fluid at a mass flow rate of about 591 kg/s to the pre-heater 104a, which repeats the Rankine cycle to generate power.

Figure 1D:
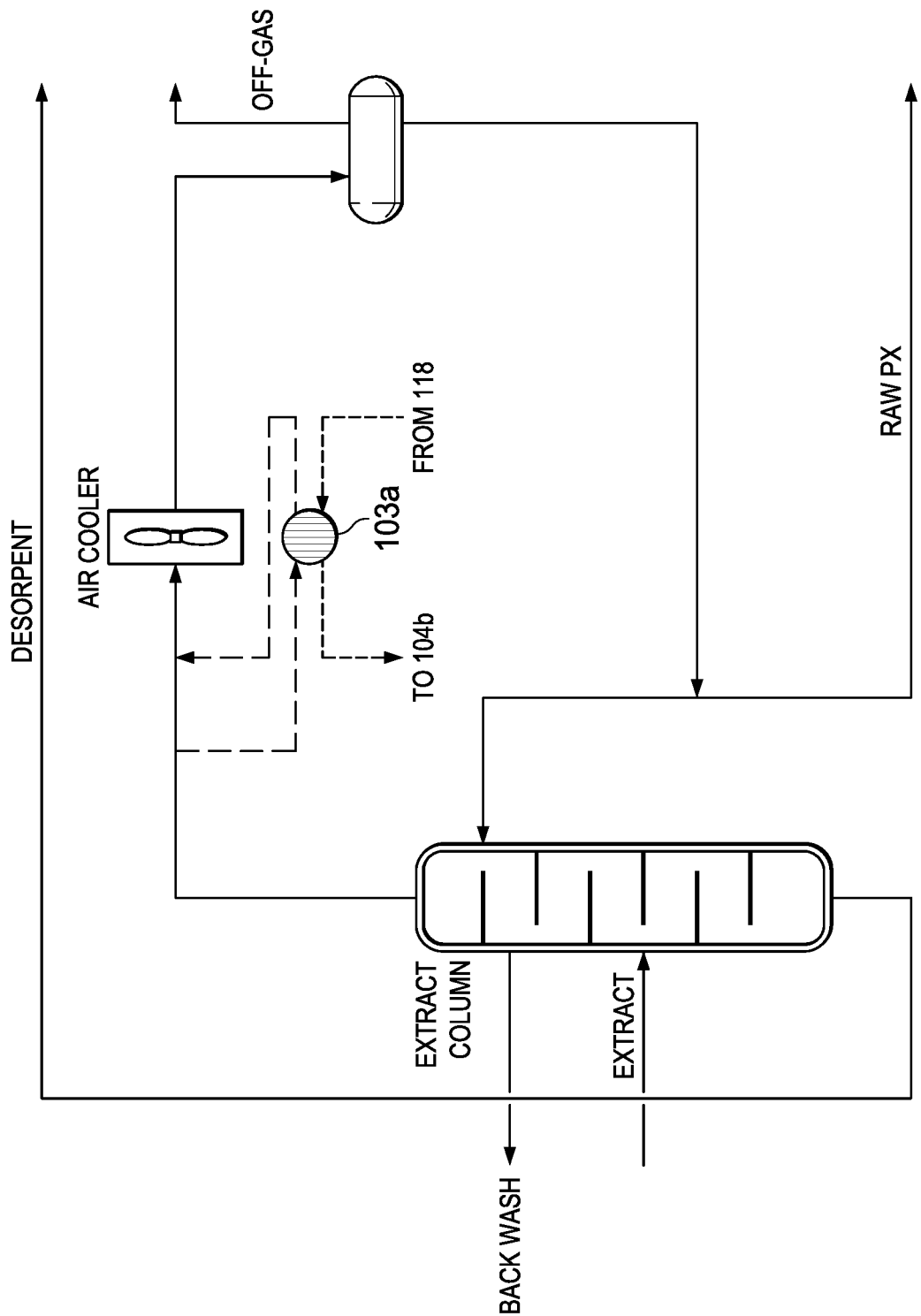
FIGS. 1D-1M are schematic diagrams of heat sources in an aromatics plant.

FIGS. 1D-1M are schematic diagrams of heat sources in an aromatics plant. FIG. 1D shows the first heat exchanger 103a in the second heating fluid circuit 103 in the aromatics plant of the petrochemical refining system. A stream from an extract column overhead and the heating fluid flow through the first heat exchanger 103a simultaneously. The first heat exchanger 103a cools down the stream from a higher temperature, for example, about 156° C., to a lower temperature, for example, about 133° C., and increases the temperature of the heating fluid from a lower temperature, for example, about 105° C., to a higher temperature, for example, about 151° C. The thermal duty of the first heat exchanger 103a to implement the heat exchange is about 33 MW. The heating fluid at about 151° C. that exits the first heat exchanger 103a is circulated to a main heater to be mixed with the heated heating fluid from the other heat exchanger in the second heating fluid circuit 103.

Figure 1E:
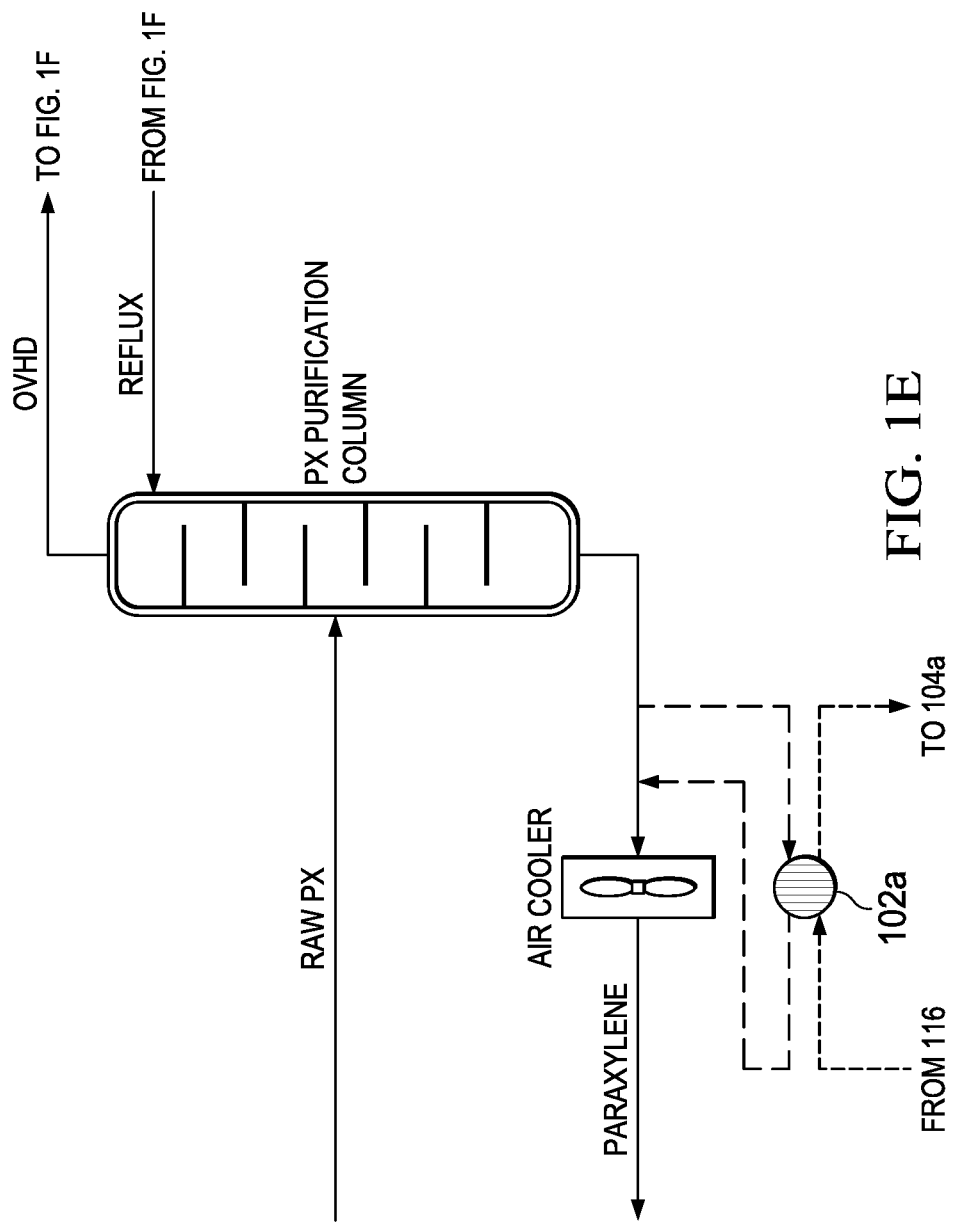

FIG. 1E shows the first heat exchanger 102a in the first heating fluid circuit 102 in the aromatics plant of the petrochemical refining system. The aromatics plant can include a para-Xylene separation plant. A stream from a para-Xylene purification column bottom product and the heating fluid flow through the first heat exchanger 102a simultaneously. The first heat exchanger 102a cools down the stream from a higher temperature, for example, about 155° C., to a lower temperature, for example, about 60° C., and increases the temperature of the heating fluid from a lower temperature, for example, about 50° C., to a higher temperature, for example, about 150° C. The thermal duty of the first heat exchanger 102a to implement the heat exchange is about 5 MW. The heating fluid at about 150° C. that exits the first heat exchanger 102a is circulated to a main heater to be mixed with the heated heating fluids from the eight other heat exchangers in the first heating fluid circuit 102.

Figure 1F:
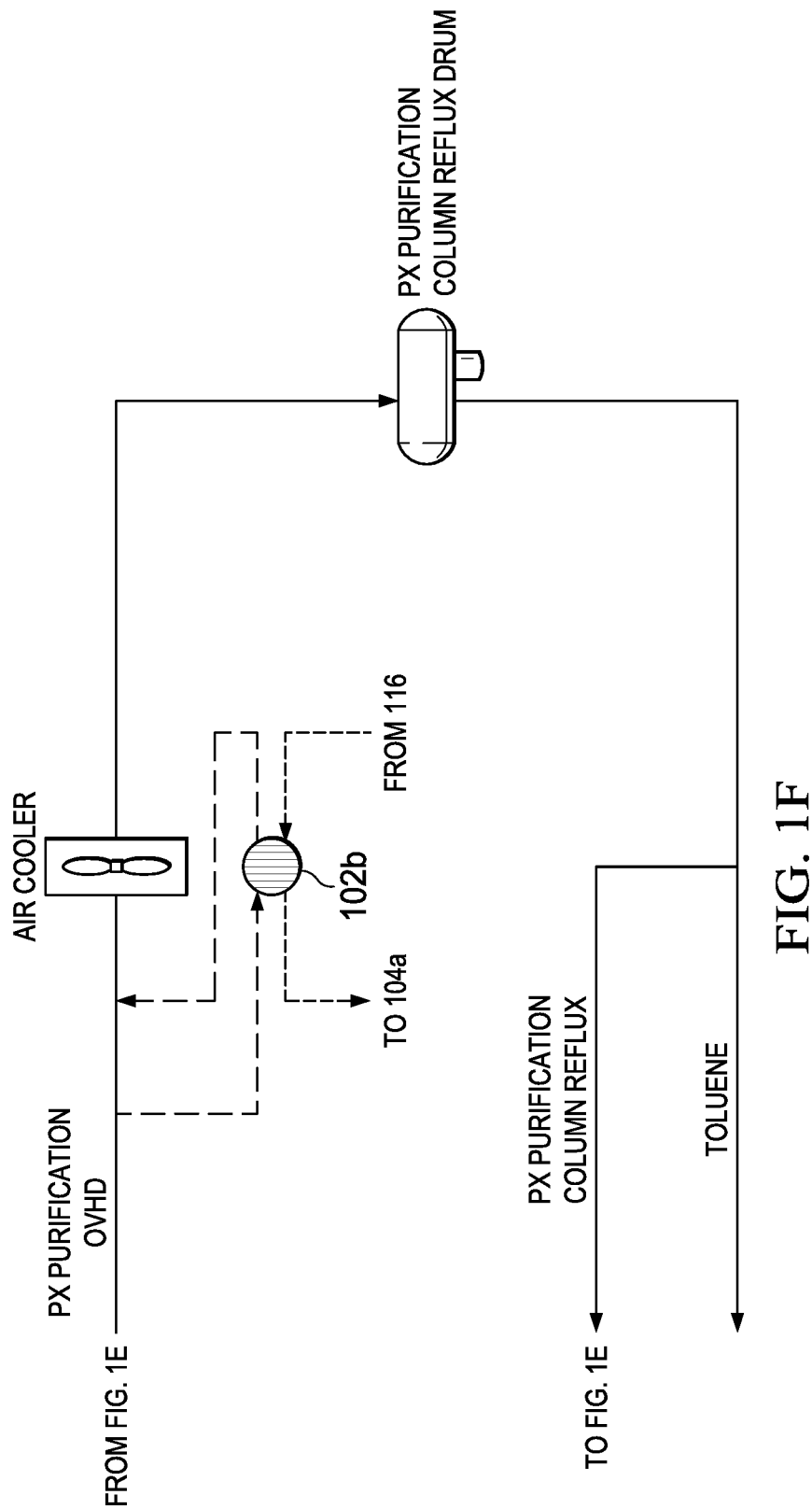

FIG. 1F shows the second heat exchanger 102b in the first heating fluid circuit 102 in the aromatics plant of the petrochemical refining system. The aromatics plant can include a para-Xylene separation plant. A stream from a para-Xylene purification column overhead and the heating fluid flow through the second heat exchanger 102b simultaneously. The second heat exchanger 102b cools down the stream from a higher temperature, for example, about 127° C., to a lower temperature, for example, about 84° C., and increases the temperature of the heating fluid from a lower temperature, for example, about 50° C., to a higher temperature, for example, about 122° C. The thermal duty of the second heat exchanger 102b to implement the heat exchange is about 14 MW. The heating fluid at about 122° C. that exits the second heat exchanger 102b is circulated to a main heater to be mixed with the heated heating fluids from the eight other heat exchangers in the first heating fluid circuit 102.

Figure 1G:
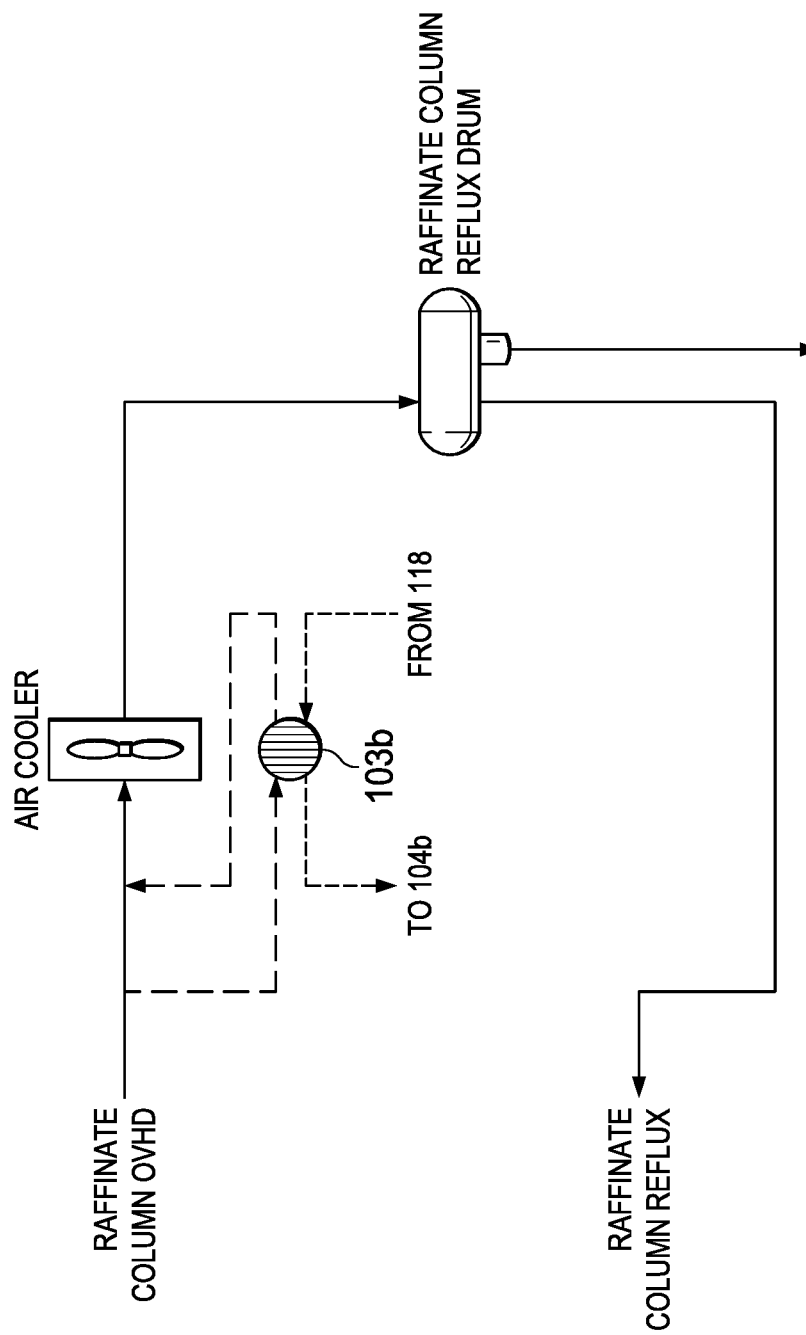

FIG. 1G shows the second heat exchanger 103b in the second heating fluid circuit 103 in the aromatics plant of the petrochemical refining system. The aromatics plant can include a para-Xylene separation plant. A stream from a Raffinate column overhead and the heating fluid flow through the second heat exchanger 103b simultaneously. The second heat exchanger 103b cools down the stream from a higher temperature, for example, about 162° C., to a lower temperature, for example, about 130° C., and increases the temperature of the heating fluid from a lower temperature, for example, about 105° C., to a higher temperature, for example, about 157° C. The thermal duty of the second heat exchanger 103b to implement the heat exchange is about 91 MW. The heating fluid at about 157° C. that exits the second heat exchanger 103b is circulated to a main heater to be mixed with the heated heating fluid from the other heat exchanger in the second heating fluid circuit 103.

Figure 1H:
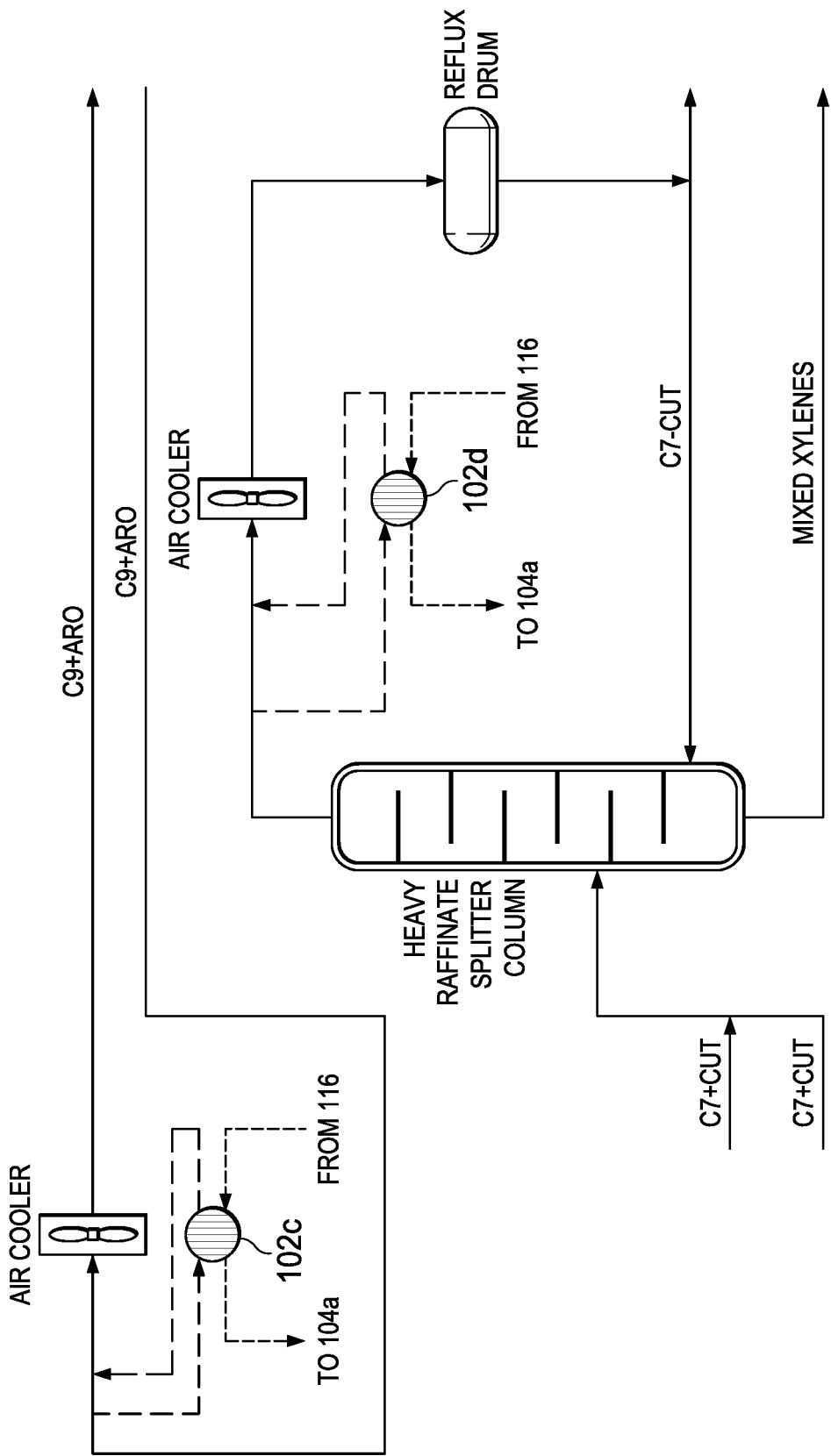

FIG. 1H shows the third heat exchanger 102c in the first heating fluid circuit 102 in the aromatics plant of the petrochemical refining system. The aromatics plant can include a C9+ aromatics unit. A stream from a C9+ aromatics unit and the heating fluid flow through the third heat exchanger 102c simultaneously. The third heat exchanger 102c cools down the stream from a higher temperature, for example, about 169° C., to a lower temperature, for example, about 60° C., and increases the temperature of the heating fluid from a lower temperature, for example, about 50° C., to a higher temperature, for example, about 164° C. The thermal duty of the third heat exchanger 102c to implement the heat exchange is about 7 MW. The heating fluid at about 164° C. that exits the third heat exchanger 102c is circulated to a main heater to be mixed with the heated heating fluids from the eight other heat exchangers in the first heating fluid circuit 102.

FIG. 1H also shows the fourth heat exchanger 102d in the first heating fluid circuit 102 in the aromatics plant of the petrochemical refining system. The aromatics plant can include a heavy Raffinate column splitter. A stream from a heavy Raffinate splitter column overhead and the heating fluid flow through the fourth heat exchanger 102d simultaneously. The fourth heat exchanger 102d cools down the stream from a higher temperature, for example, about 126° C., to a lower temperature, for example, about 113° C., and increases the temperature of the heating fluid from a lower temperature, for example, about 50° C., to a higher temperature, for example, about 121° C. The thermal duty of the fourth heat exchanger 102d to implement the heat exchange is about 32 MW. The heating fluid at about 121° C. that exits the fourth heat exchanger 102d is circulated to a main heater to be mixed with the heated heating fluids from the eight other heat exchangers in the first heating fluid circuit 102.

Figure 1I:
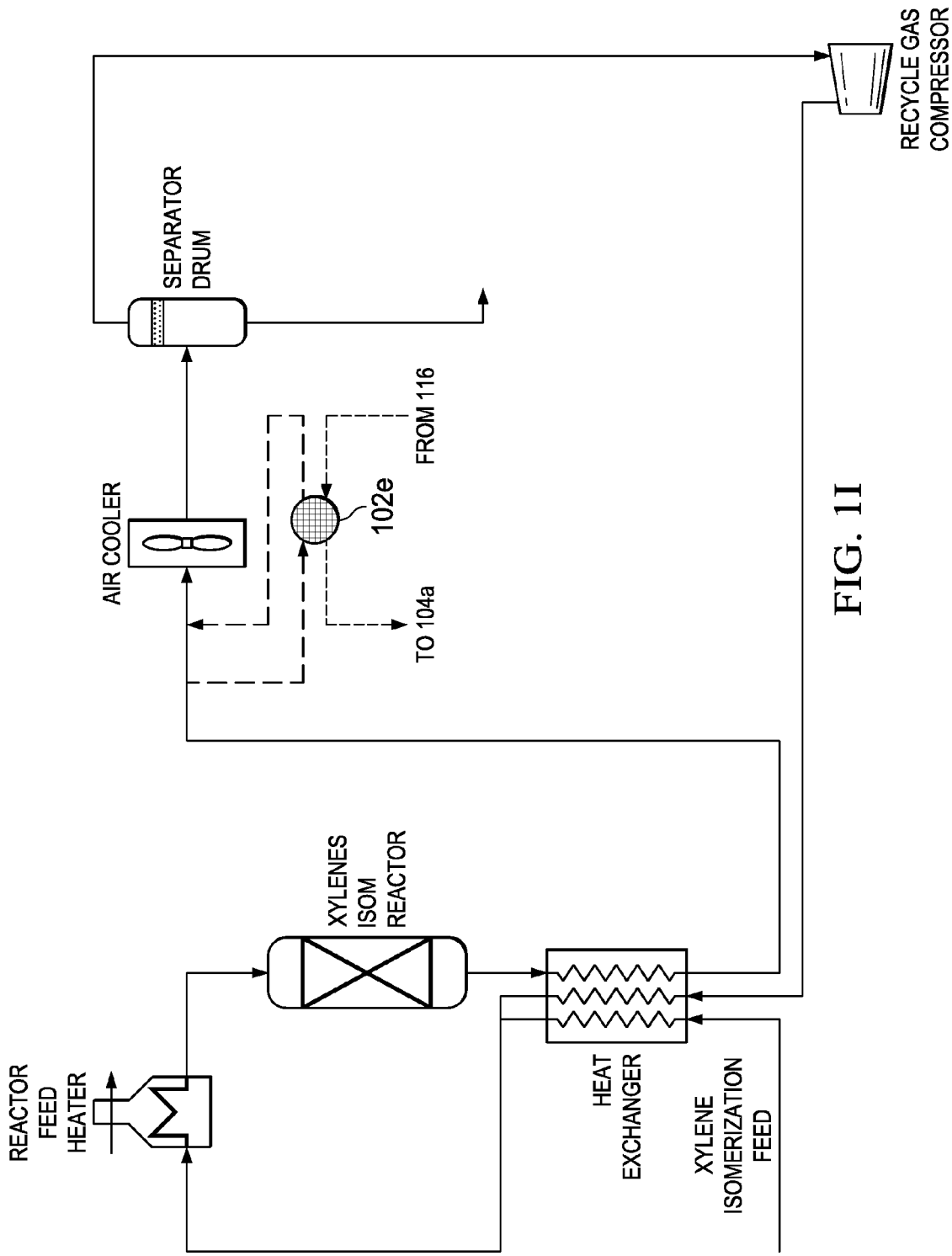

FIG. 1I shows the fifth heat exchanger 102e in the first heating fluid circuit 102 in the aromatics plant of the petrochemical refining system. The aromatics plant can include a Xylene isomerization reactor. A stream from a Xylene isomerization reactor outlet and the heating fluid flow through the fifth heat exchanger 102e simultaneously. The fifth heat exchanger 102e cools down the stream from a higher temperature, for example, about 114° C., to a lower temperature, for example, about 47° C., and increases the temperature of the heating fluid from a lower temperature, for example, about 50° C., to a higher temperature, for example, about 109° C. The thermal duty of the fifth heat exchanger 102e to implement the heat exchange is about 16 MW. The heating fluid at about 109° C. that exits the fifth heat exchanger 102e is circulated to a main heater to be mixed with the heated heating fluids from the eight other heat exchangers in the first heating fluid circuit 102.

Figure 1J:
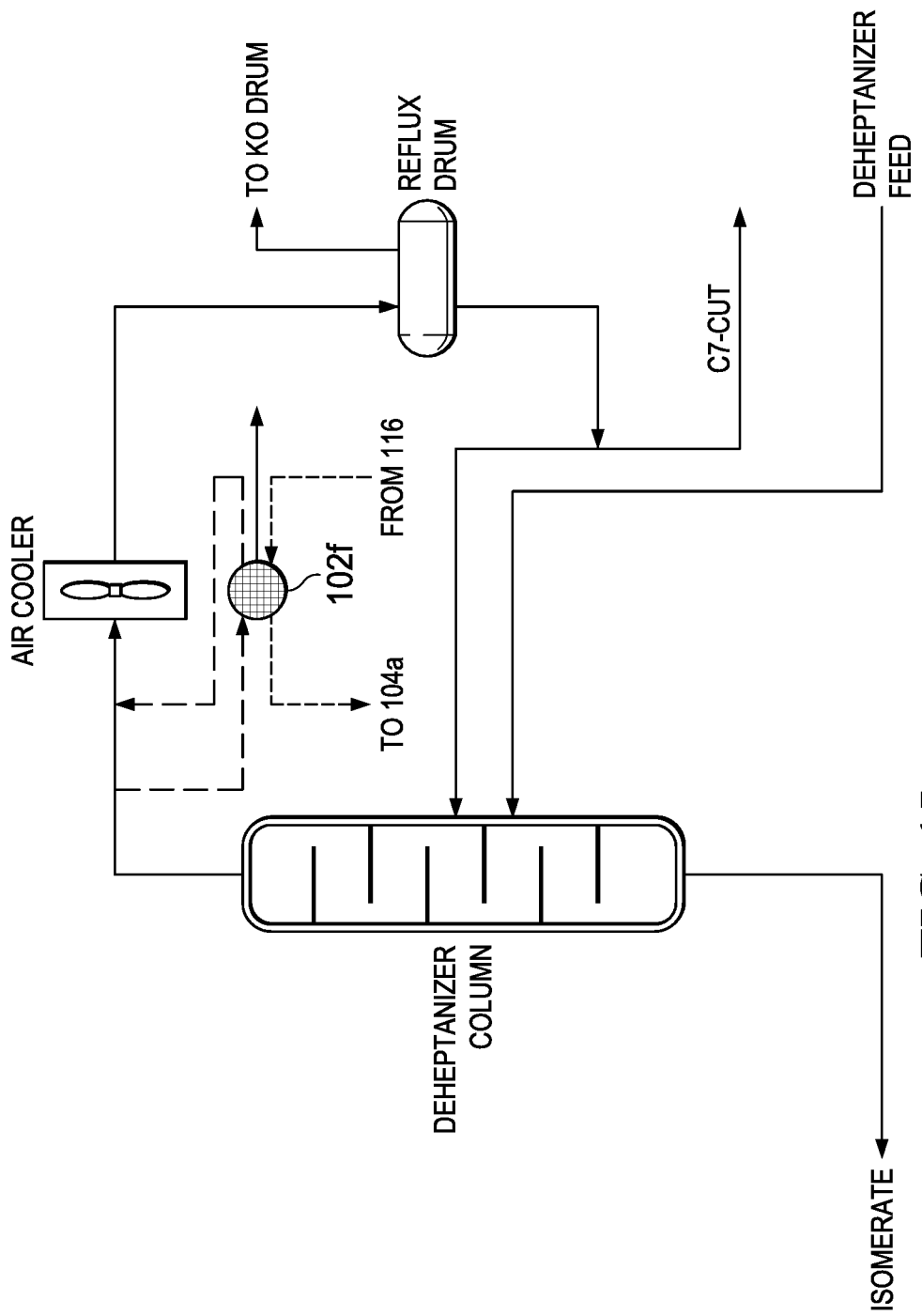

FIG. 1J shows the sixth heat exchanger 102f in the first heating fluid circuit 102 in the aromatics plant of the petrochemical refining system. The aromatics plant can include a Xylene isomerization de-heptanizer. A stream from a Xylene isomerization de-heptanizer column overhead and the heating fluid flow through the sixth heat exchanger 102f simultaneously. The sixth heat exchanger 102f cools down the stream from a higher temperature, for example, about 112° C., to a lower temperature, for example, about 59° C., and increases the temperature of the heating fluid from a lower temperature, for example, about 50° C., to a higher temperature, for example, about 107° C. The thermal duty of the sixth heat exchanger 102f to implement the heat exchange is about 21 MW. The heating fluid at about 107°

C. that exits the sixth heat exchanger 102f is circulated to a main heater to be mixed with the heated heating fluids from the eight other heat exchangers in the first heating fluid circuit 102.

Figure 1K:
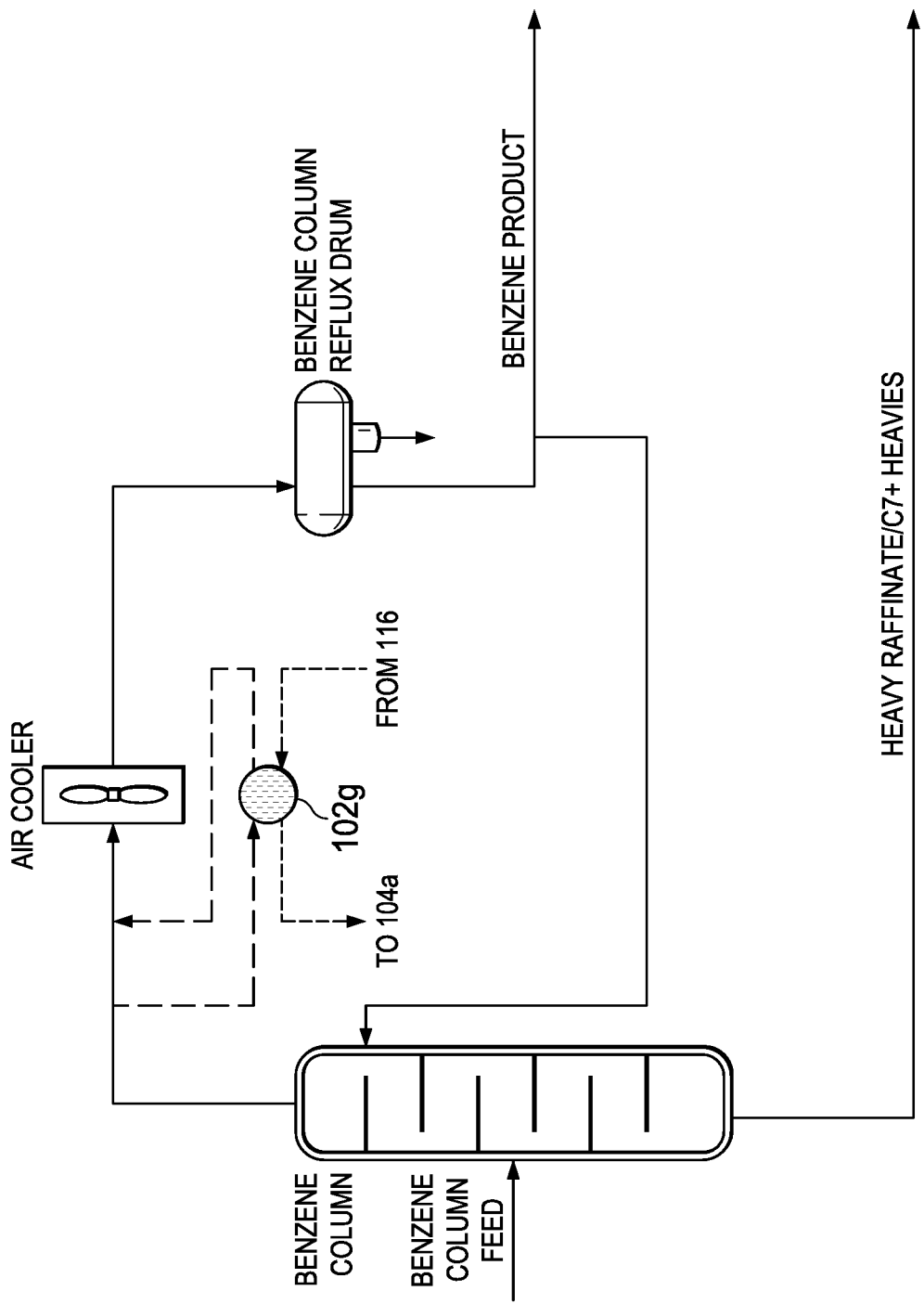

FIG. 1K shows the seventh heat exchanger 102g in the first heating fluid circuit 102 in the aromatics plant of the petrochemical refining system. The aromatics plant can include an aromatics benzene extraction unit. A stream from a benzene column overhead and the heating fluid flow through the seventh heat exchanger 102g simultaneously. The seventh heat exchanger 102g cools down the stream from a higher temperature, for example, about 104° C., to a lower temperature, for example, about 100° C., and increases the temperature of the heating fluid from a lower temperature, for example, about 50° C., to a higher temperature, for example, about 99° C. The thermal duty of the seventh heat exchanger 102g to implement the heat exchange is about 5 MW. The heating fluid at about 99° C. that exits the seventh heat exchanger 102g is circulated to a main heater to be mixed with the heated heating fluids from the eight other heat exchangers in the first heating fluid circuit 102.

Figure 1L:
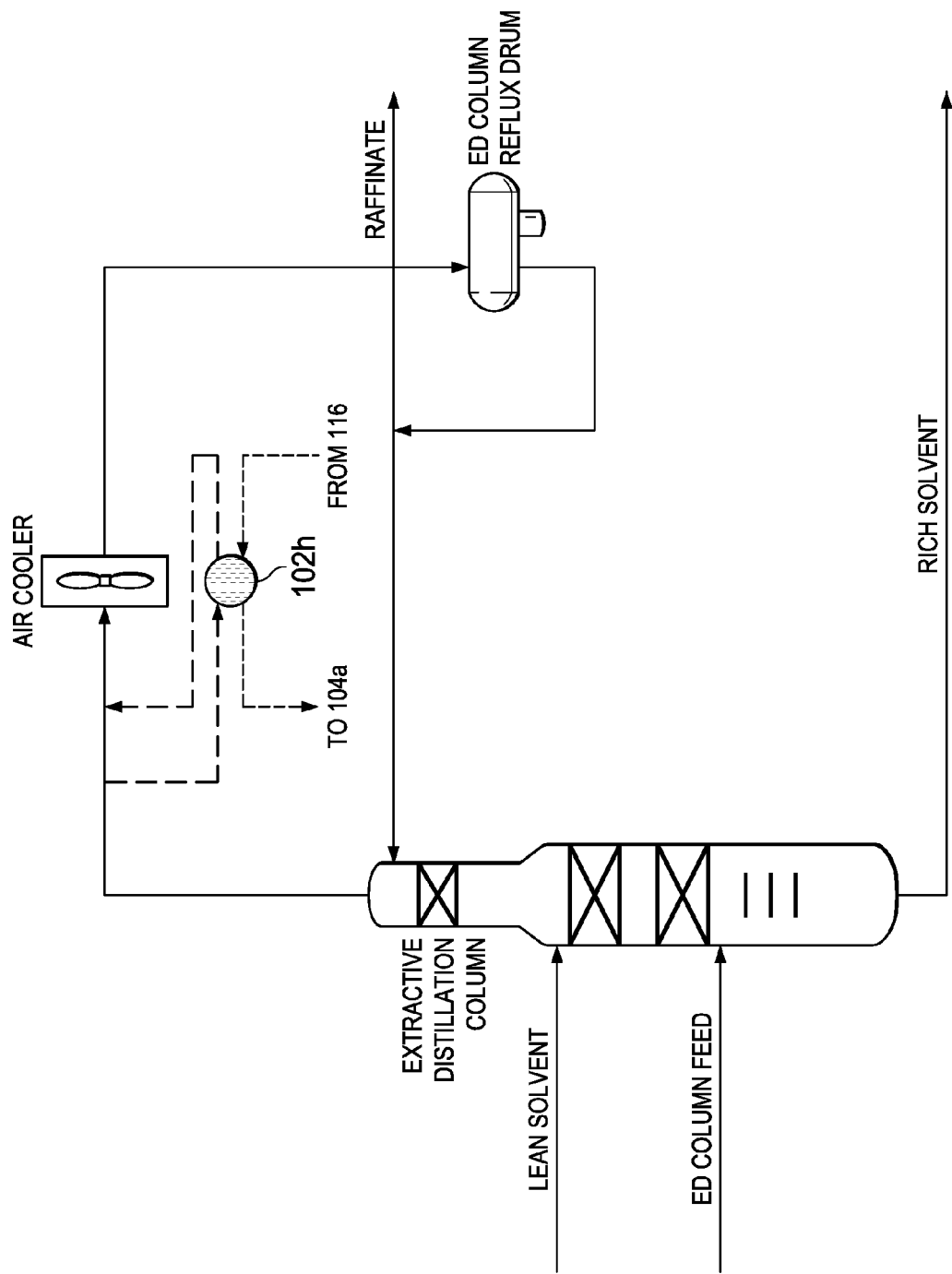

FIG. 1L shows the eighth heat exchanger 102h in the first heating fluid circuit 102 in the aromatics plant of the petrochemical refining system. The aromatics plant can include an aromatics complex extractive distillation column unit. A stream from an extractive distillation column overhead and the heating fluid flow through the eighth heat exchanger 102h simultaneously. The eighth heat exchanger 102h cools down the stream from a higher temperature, for example, about 92° C., to a lower temperature, for example, about 73° C., and increases the temperature of the heating fluid from a lower temperature, for example, about 50° C., to a higher temperature, for example, about 87° C. The thermal duty of the eighth heat exchanger 102h to implement the heat exchange is about 8 MW. The heating fluid at about 87° C. that exits the eighth heat exchanger 102h is circulated to a main heater to be mixed with the heated heating fluids from the eight other heat exchangers in the first heating fluid circuit 102.

Figure 1M:
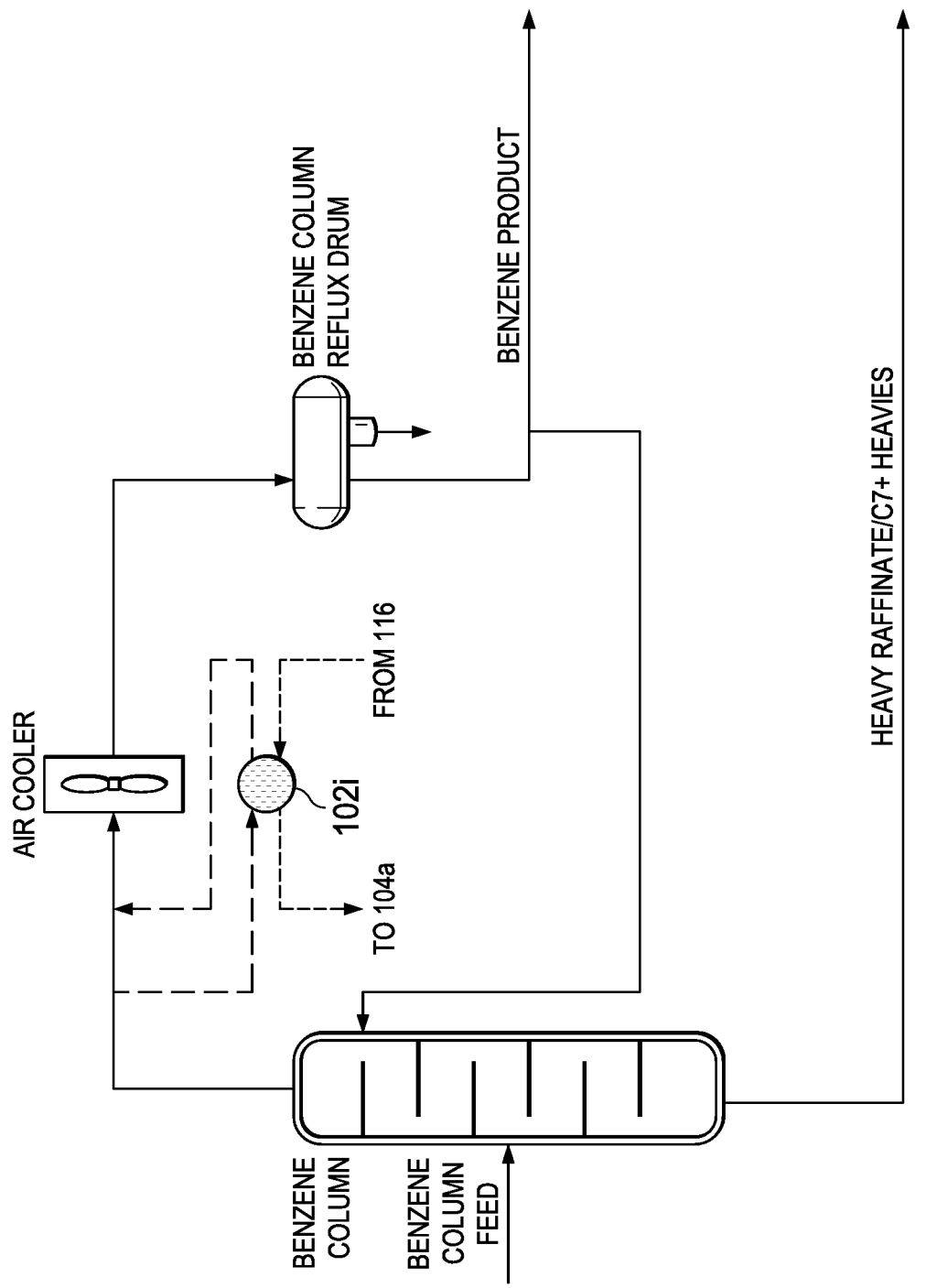
Figure 1N:
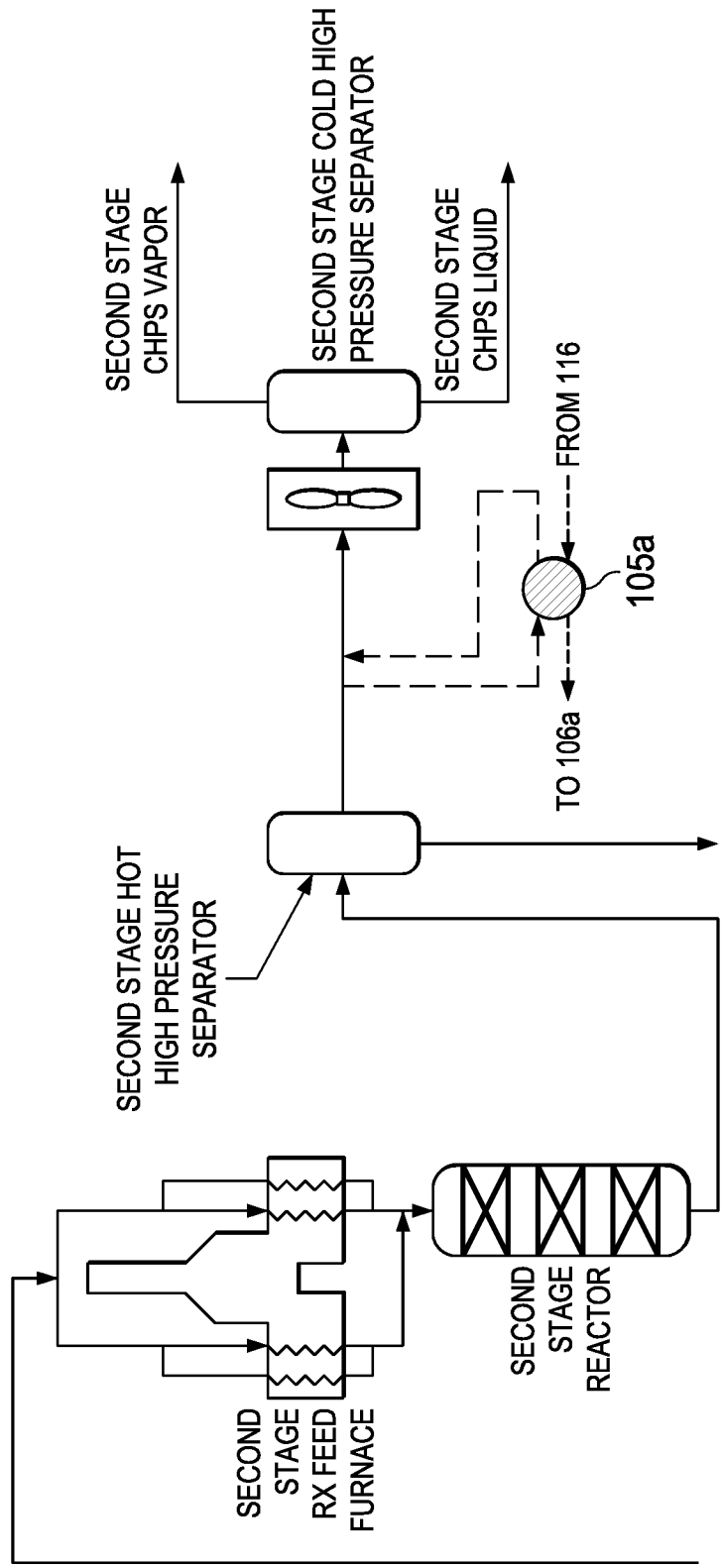
FIGS. 1N-1P are schematic diagrams of heat sources in a hydrocracking plant.
Figure 1O:
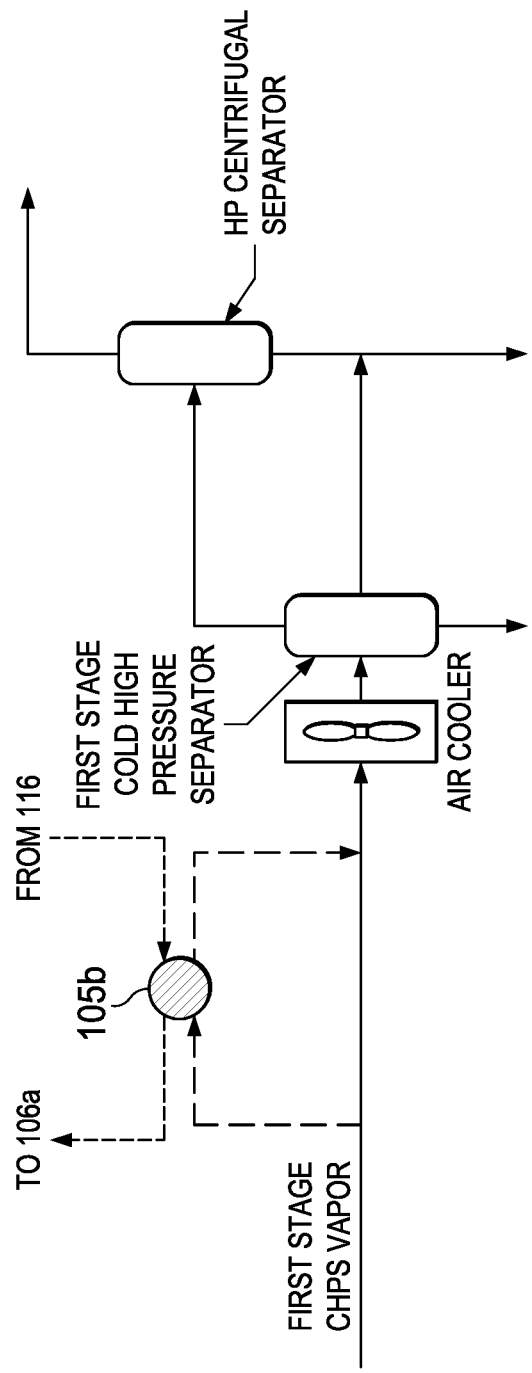
Figure 1P:
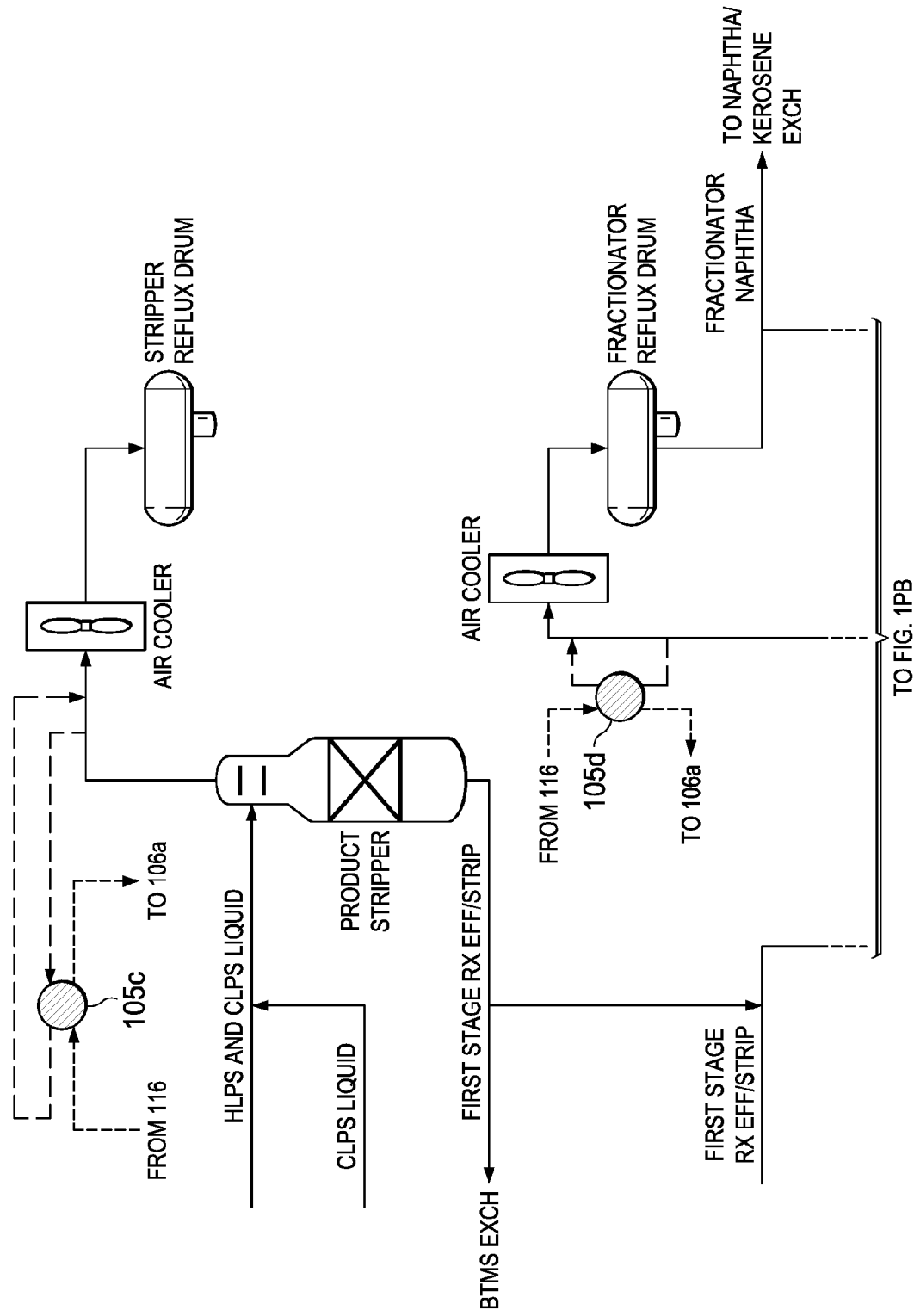
Figure 1P:
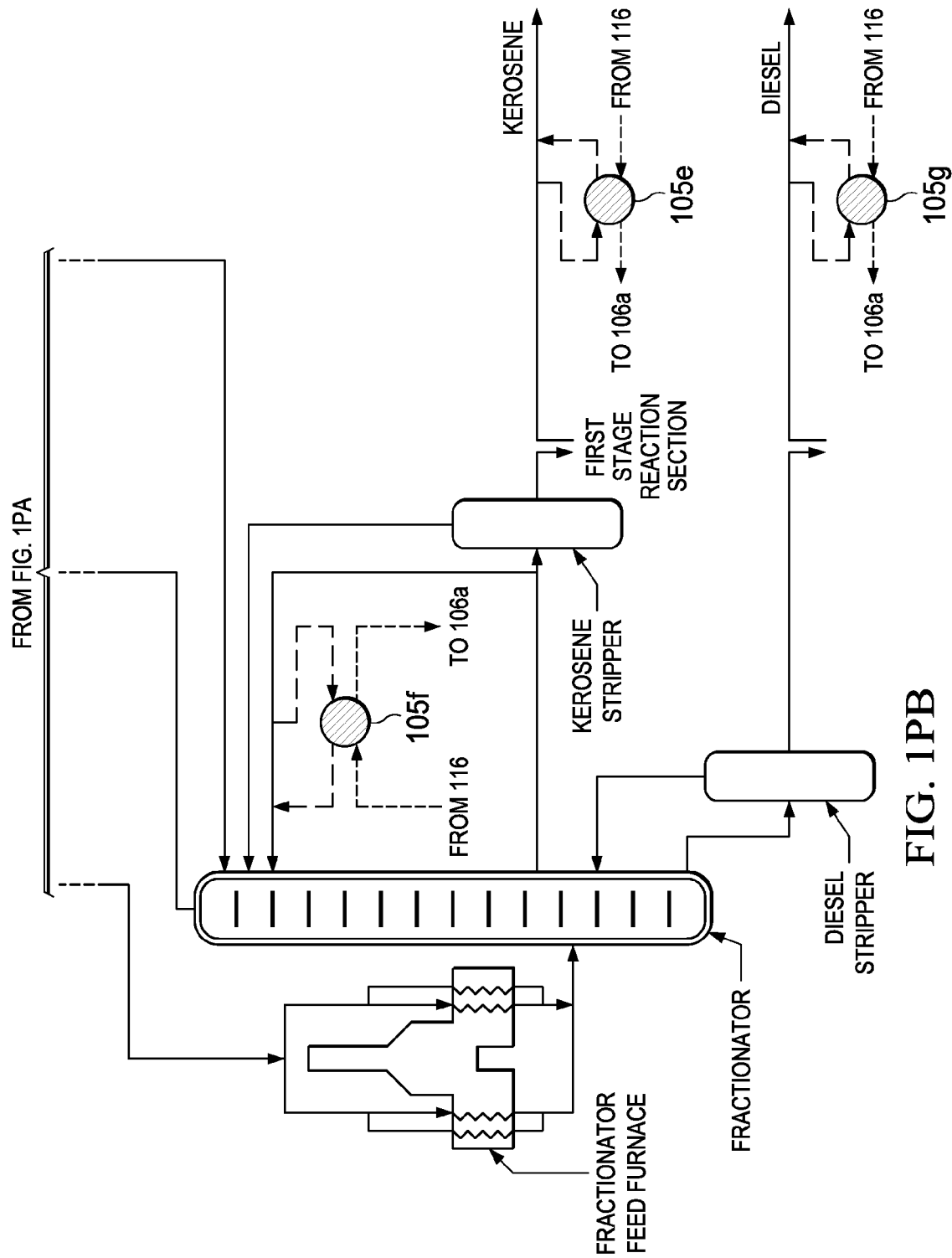
Figure 1Q:
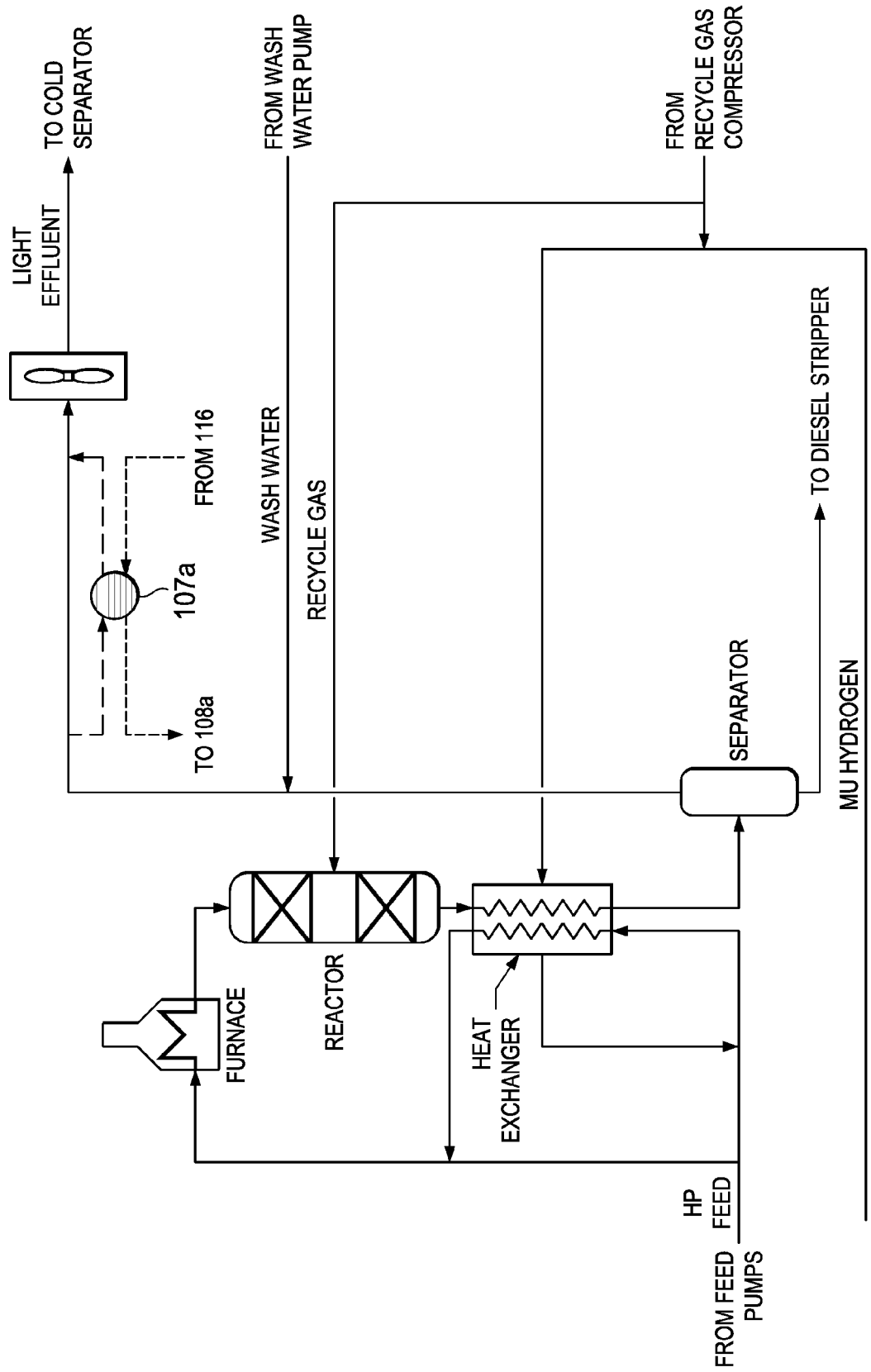
FIGS. 1Q and 1R are schematic diagrams of heat sources in a diesel hydro-treating plant.
Figure 1R:
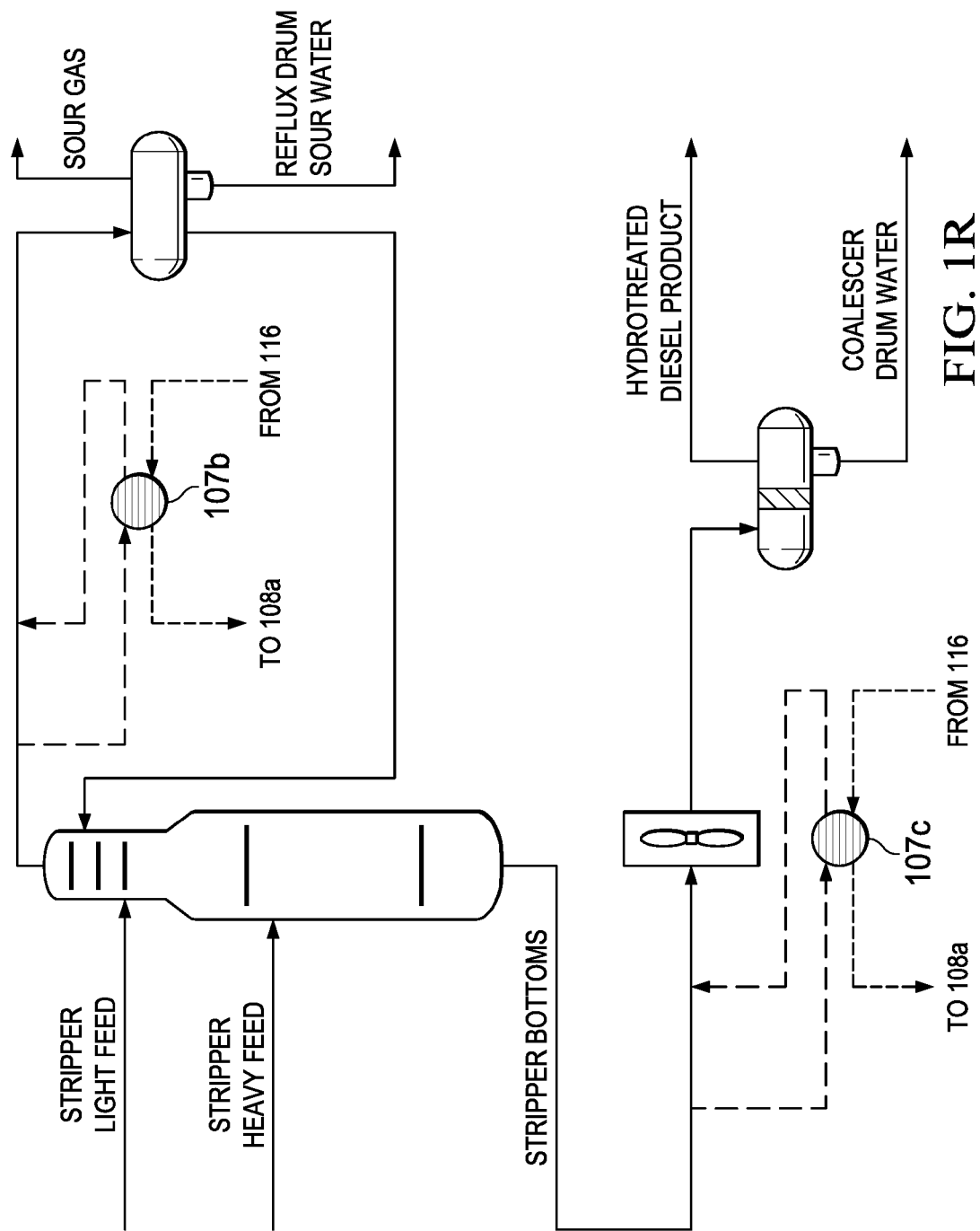

FIG. 1M shows the ninth heat exchanger 102i in the first heating fluid circuit 102 in the aromatics plant of the petrochemical refining system. The aromatics plant can include an aromatics complex Raffinate splitter. A stream from a Raffinate splitter overhead and the heating fluid flow through the ninth heat exchanger 102i simultaneously. The ninth heat exchanger 102i cools down the stream from a higher temperature, for example, about 76° C., to a lower temperature, for example, about 60° C., and increases the temperature of the heating fluid from a lower temperature, for example, about 50° C., to a higher temperature, for example, about 71° C. The thermal duty of the ninth heat exchanger 102i to implement the heat exchange is about 9 MW. The heating fluid at about 71° C. that exits the ninth heat exchanger 102i is circulated to a main heater to be mixed with the heated heating fluids from the eight other heat exchangers in the first heating fluid circuit 102.

The heating fluids received from the seven heat exchangers in the third heating circuit are mixed in the main header resulting in a heating fluid at a temperature of about 156° C. The heated heating fluid from the third heating fluid circuit 105 is circulated through the evaporator 106a of the ORC of the second power generation system 106. In some implementations, the evaporator 106a increase the temperature of the working fluid (for example, isobutane or other working fluid) from about 31° C. at about 20 bar to about 99° C. at about 20 bar at a thermal duty of about 257 MW. The gas expander 106b expands the high temperature, high pressure working fluid to generate power, for example, about 32 MW, at an efficiency of about 85%. The expansion decreases the temperature and pressure of the working fluid, for example, to about 52° C. and about 4.3 bar, respectively. The working fluid flows through the condenser 106c which further decreases the temperature and pressure of the working fluid at a thermal duty of about 228 MW. For example, cooling fluid flows through the condenser 106c at a lower temperature, for example, about 20° C., exchanges heat with the working fluid, and exits the condenser 106c at a higher temperature, for example, about 30° C. The cooled working fluid (for example, isobutane liquid) is pumped by the pump 106d at an efficiency, for example, of about 75%, and an input power, for example, of about 3 MW. The pump 106d increases the temperature of the working fluid to about 31° C. and pumps the working fluid at a mass flow rate of about 630 kg/s to the evaporator 106a, which repeats the Rankine cycle to generate power.

FIGS. 1N, 1O, and 1PA and 1PB (collectively, FIG. 1P) are schematic diagrams of heat sources in a hydrocracking plant. FIG. 1N shows the first heat exchanger 105a in the third heating fluid circuit 105 in the hydrocracking plant of the petrochemical refining system. A stream from a hydrocracking $2^{nd}$ stage reaction section feed to $2^{nd}$ stage cold high pressure separator and the heating fluid flow through the first heat exchanger 105a simultaneously. The first heat exchanger 105a cools down the stream from a higher temperature, for example, about 157° C., to a lower temperature, for example, about 60° C., and increases the temperature of the heating fluid from a lower temperature, for example, about 50° C., to a higher temperature, for example, about 152° C. The thermal duty of the first heat exchanger 105a to implement the heat exchange is about 26 MW. The heating fluid at about 152° C. that exits the first heat exchanger 105a is circulated to a main heater to be mixed with the heated heating fluid from the other heat exchangers in the third heating fluid circuit 105.

FIG. 1O shows the second heat exchanger 105b in the third heating fluid circuit 105 in the hydrocracking plant of the petrochemical refining system. A stream from a hydrocracking $1^{st}$ stage reaction section feed to $1_{st}$ stage cold high pressure separator and the heating fluid flow through the first heat exchanger 105a simultaneously. The second heat exchanger 105b cools down the stream from a higher temperature, for example, about 159° C., to a lower temperature, for example, about 60° C., and increases the temperature of the heating fluid from a lower temperature, for example, about 50° C., to a higher temperature, for example, about 154° C. The thermal duty of the second heat exchanger 105b to implement the heat exchange is about 82 MW. The heating fluid at about 154° C. that exits the second heat exchanger 105b is circulated to a main heater to be mixed with the heated heating fluid from the other heat exchangers in the third heating fluid circuit 105.

FIG. 1P shows the fifth heat exchanger 105e in the third heating fluid circuit 105 in the hydrocracking plant of the petrochemical refining system. A stream from a hydrocracking main fractionator kerosene product after steam generation and the heating fluid flow through the fifth heat exchanger 105e simultaneously. The fifth heat exchanger 105e cools down the stream from a higher temperature, for example, about 160° C., to a lower temperature, for example, about 60° C., and increases the temperature of the heating fluid from a lower temperature, for example, about 50° C., to a higher temperature, for example, about 155° C. The thermal duty of the fifth heat exchanger 105e to implement the heat exchange is about 20 MW. The heating fluid at about 155° C. that exits the fifth heat exchanger 105e is circulated to a main heater to be mixed with the heated heating fluid from the other heat exchangers in the third heating fluid circuit 105.

FIG. 1P also shows the seventh heat exchanger 105g in the third heating fluid circuit 105 in the hydrocracking plant of the petrochemical refining system. A stream from a hydrocracking main fractionator diesel product after steam generation and the heating fluid flow through the seventh heat exchanger 105g simultaneously. The seventh heat exchanger 105g cools down the stream from a higher temperature, for example, about 160° C., to a lower temperature, for example, about 121° C., and increases the temperature of the heating fluid from a lower temperature, for example, about 50° C., to a higher temperature, for example, about 155° C. The thermal duty of the seventh heat exchanger 105g to implement the heat exchange is about 6 MW. The heating fluid at about 155° C. that exits the seventh heat exchanger 105g is circulated to a main heater to be mixed with the heated heating fluid from the other heat exchangers in the third heating fluid circuit 105.

FIG. 1P additionally shows the third heat exchanger 105c in the third heating fluid circuit 105 in the hydrocracking plant of the petrochemical refining system. A stream from a hydrocracking product stripper overhead and the heating fluid flow through the third heat exchanger 105c simultaneously. The third heat exchanger 105c cools down the stream from a higher temperature, for example, about 169° C., to a lower temperature, for example, about 60° C., and increases the temperature of the heating fluid from a lower temperature, for example, about 50° C., to a higher temperature, for example, about 164° C. The thermal duty of the third heat exchanger 105c to implement the heat exchange is about 37 MW. The heating fluid at about 164° C. that exits the third heat exchanger 105c is circulated to a main heater to be mixed with the heated heating fluid from the other heat exchangers in the third heating fluid circuit 105.

FIG. 1P further shows the fourth heat exchanger 105d in the third heating fluid circuit 105 in the hydrocracking plant of the petrochemical refining system. A stream from a hydrocracking main fractionator overhead and the heating fluid flow through the fourth heat exchanger 105d simultaneously. The fourth heat exchanger 105d cools down the stream from a higher temperature, for example, about 136° C., to a lower temperature, for example, about 60° C., and increases the temperature of the heating fluid from a lower temperature, for example, about 50° C., to a higher temperature, for example, about 131° C. The thermal duty of the fourth heat exchanger 105d to implement the heat exchange is about 89 MW. The heating fluid at about 131° C. that exits the fourth heat exchanger 105d is circulated to a main heater to be mixed with the heated heating fluid from the other heat exchangers in the third heating fluid circuit 105.

FIG. 1P shows the sixth heat exchanger 105f in the third heating fluid circuit 105 in the hydrocracking plant of the petrochemical refining system. A stream from a hydrocracking main fractionator kerosene pumparound and the heating fluid flow through the sixth heat exchanger 105f simultaneously. The sixth heat exchanger 105f cools down the stream from a higher temperature, for example, about 160° C., to a lower temperature, for example, about 130° C., and increases the temperature of the heating fluid from a lower temperature, for example, about 50° C., to a higher temperature, for example, about 155° C. The thermal duty of the sixth heat exchanger 105f to implement the heat exchange is about 5 MW. The heating fluid at about 155° C. that exits the sixth heat exchanger 105f is circulated to a main heater to be mixed with the heated heating fluid from the other heat exchangers in the third heating fluid circuit 105.

FIGS. 1Q and 1R are schematic diagrams of heat sources in a diesel hydro-treating plant. FIG. 1Q shows the first heat exchanger 107a in the fourth heating fluid circuit 107 in the diesel hydro-treating plant of the petrochemical refining system. A stream from a light effluent to cold separator and the heating fluid flow through the first heat exchanger 107a simultaneously. The first heat exchanger 107a cools down the stream from a higher temperature, for example, about 127° C., to a lower temperature, for example, about 60° C., and increases the temperature of the heating fluid from a lower temperature, for example, about 50° C., to a higher temperature, for example, about 122° C. The thermal duty of the first heat exchanger 107a to implement the heat exchange is about 23 MW. The heating fluid at about 122° C. that exits the first heat exchanger 107a is circulated to a main heater to be mixed with the heated heating fluid from the two other heat exchangers in the fourth heating fluid circuit 107.

FIG. 1R shows the second heat exchanger 107b in the fourth heating fluid circuit 107 in the diesel hydro-treating plant of the petrochemical refining system. A stream from a diesel stripper overhead and the heating fluid flow through the second heat exchanger 107b simultaneously. The second heat exchanger 107b cools down the stream from a higher temperature, for example, about 160° C., to a lower temperature, for example, about 60° C., and increases the temperature of the heating fluid from a lower temperature, for example, about 50° C., to a higher temperature, for example, about 155° C. The thermal duty of the second heat exchanger 107b to implement the heat exchange is about 34 MW. The heating fluid at about 155° C. that exits the second heat exchanger 107b is circulated to a main heater to be mixed with the heated heating fluid from the two other heat exchangers in the fourth heating fluid circuit 107.

FIG. 1R also shows the third heat exchanger 107c in the fourth heating fluid circuit 107 in the diesel hydro-treating plant of the petrochemical refining system. A stream from a diesel stripper product and the heating fluid flow through the third heat exchanger 107c simultaneously. The third heat exchanger 107c cools down the stream from a higher temperature, for example, about 162° C., to a lower temperature, for example, about 60° C., and increases the temperature of the heating fluid from a lower temperature, for example, about 50° C., to a higher temperature, for example, about 157° C. The thermal duty of the third heat exchanger 107c to implement the heat exchange is about 61 MW. The heating fluid at about 157° C. that exits the third heat exchanger 107c is circulated to a main heater to be mixed with the heated heating fluid from the two other heat exchangers in the fourth heating fluid circuit 107.

The heating fluids received from the three heat exchangers in the fourth heating fluid circuit 107 are mixed in the main header resulting in a heating fluid at a temperature of about 147° C. The heated heating fluid from the fourth heating fluid circuit 107 is circulated through the evaporator 108a of the ORC of the third power generation system 108. In some implementations, the evaporator 108a increases the temperature of the working fluid (for example, isobutane or other working fluid) from about 31° C. at about 20 bar to about 99° C. at about 20 bar at a thermal duty of about 105 MW. The gas expander 108b expands the high temperature, high pressure working fluid to generate power, for example, about 13 MW, at an efficiency of about 85%. The expansion decreases the temperature and pressure of the working fluid, for example, to about 52° C. and about 4.3 bar, respectively. The working fluid flows through the condenser 108c which further decreases the temperature and pressure of the working fluid at a thermal duty of about 93 MW. For example, cooling fluid flows through the condenser 108c at a lower temperature, for example, about 20° C., exchanges heat with the working fluid, and exits the condenser 106c at a higher temperature, for example, about 30° C. The cooled working fluid (for example, isobutane liquid) is pumped by the pump 108d at an efficiency, for example, of about 75%, and an input power, for example, of about 1 MW. The pump 108d increases the temperature of the working fluid to about 31° C. and pumps the working fluid at a mass flow rate of about 258 kg/s to the evaporator 108a, which repeats the Rankine cycle to generate power.

Figure 1S:
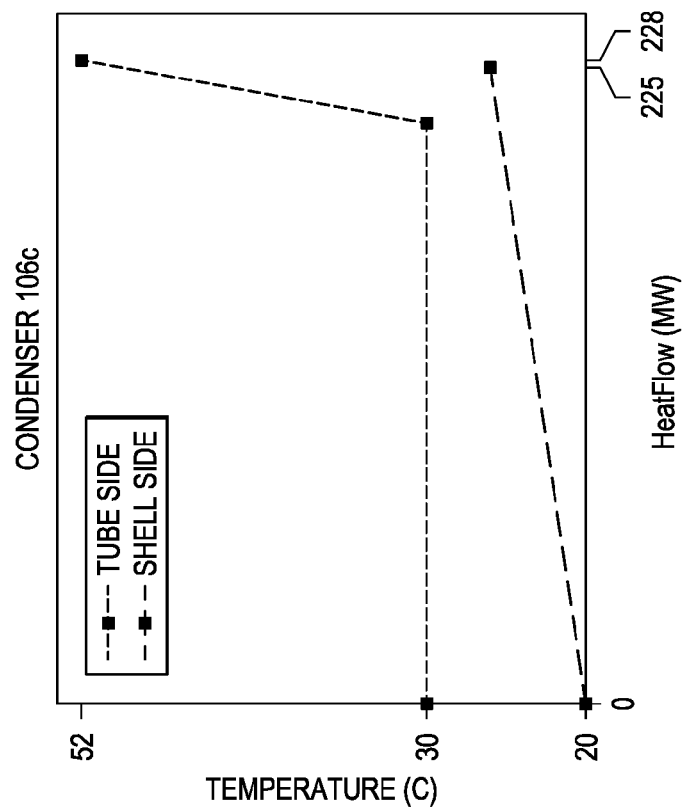
FIGS. 1SA-1SC are graphs that show a tube side fluid temperature and a shell side fluid temperature in respective condensers during an operation of the network of FIGS. 1A, 1B, and 1C.
Figure 1S:
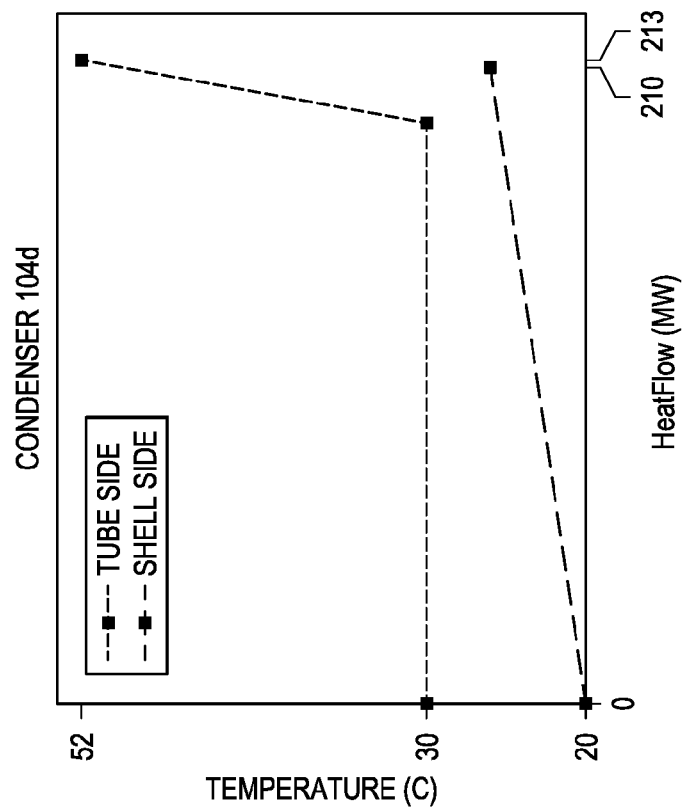
Figure 1S:
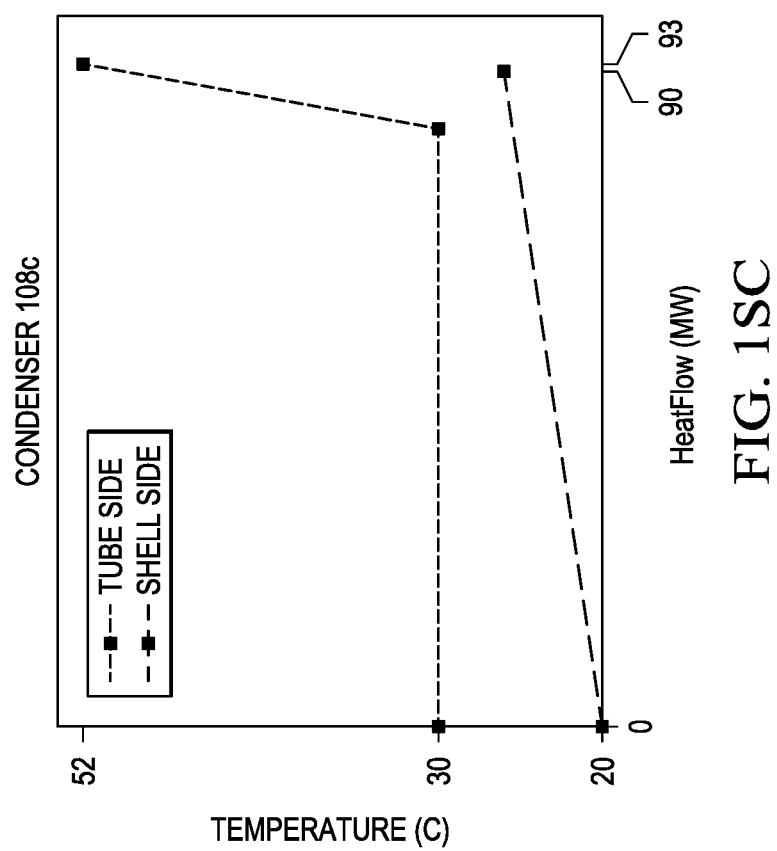

FIGS. 1SA-1SC are graphs that show a tube side fluid temperature (for example, a cooling, or condenser, fluid flow) and a shell side fluid temperature (for example, an ORC working fluid flow) in the condensers 104d, 106c, and 108c, respectively, during an operation of the system 100. This graph shows a temperature difference between the fluids on the y-axis relative to a heat flow between the fluids on the x-axis. For example, as shown in this figure, as the temperature difference between the fluids decreases, a heat flow between the fluids can increase. In some aspects, the cooling fluid medium may be at or about 20° C. or even higher. In such cases, a gas expander outlet pressure (for example, pressure of the ORC working fluid exiting the gas expander) may be high enough to allow the condensation of the ORC working fluid at the available cooling fluid temperature.

As shown in these figures, the condenser water (entering the tubes of the condensers 104d, 106c, and 108c) enters at about 20° C. and leaves at about 25-27° C. The ORC working fluid (entering the shell side of the condensers) enters as a vapor at about 52° C., and then condenses at 30° C. and leaves the condensers as a liquid at 30° C.

Figure 1T:
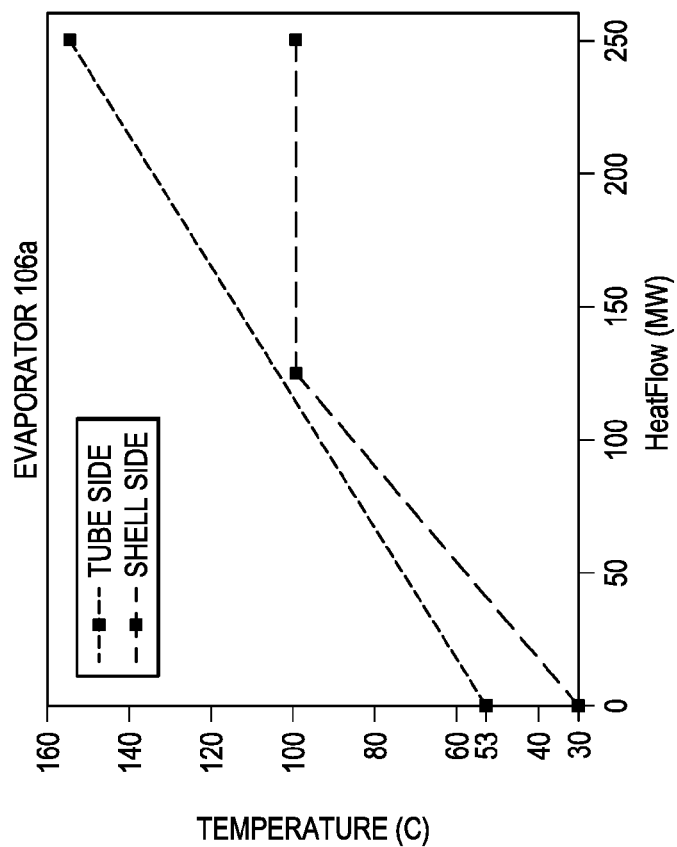
FIGS. 1TA-1TC are graphs that show a tube side fluid temperature and a shell side fluid temperature in respective evaporators during an operation of the network of FIGS. 1A, 1B, and 1C.
Figure 1T:
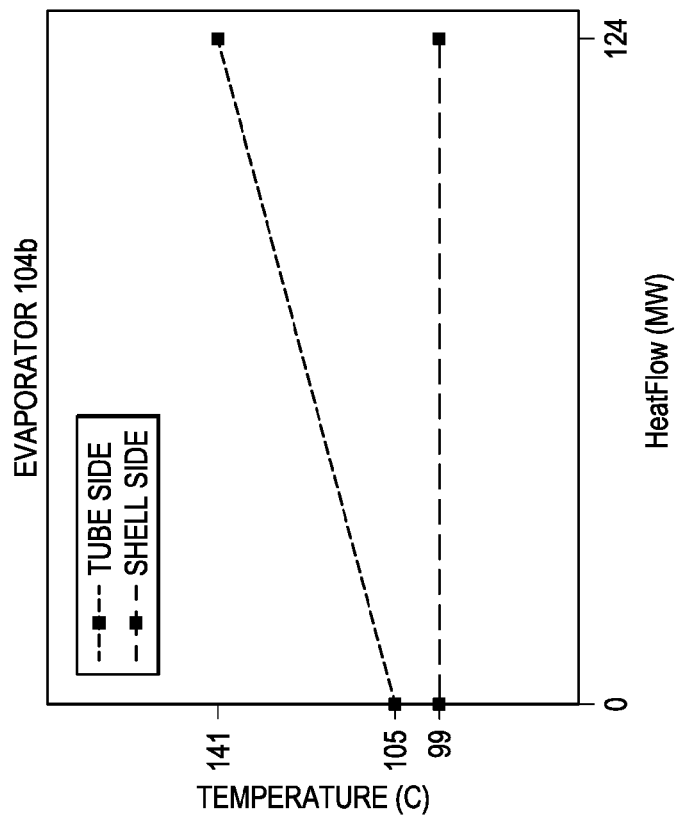

FIGS. 1TA-1TC are graphs that show a tube side fluid temperature (for example, a heating fluid flow) and a shell side fluid temperature (for example, an ORC working fluid flow) in the evaporators 104b, 106a, and 108a, respectively during an operation of the system 100. These graphs show a temperature difference between the fluids on the y-axis relative to a heat flow between the fluids on the x-axis. For example, as shown in these figures, as the temperature difference between the fluids decreases, a heat flow between the fluids can increase. These graphs each show a temperature difference between the fluids on the y-axis relative to a heat flow between the fluids on the x-axis. For example, as shown in FIG. 1TA, as the tube side fluid (for example, the hot oil or water in the heating fluid circuit 103) is circulated through the evaporator 104b, heat is transferred from that fluid to the shell side fluid (for example, the ORC working fluid). Thus, the tube side fluid enters the evaporator 104b at about 141° C. and leaves the evaporator 104b at about 105° C. The shell side fluid enters the evaporator 104b, from the pre-heater 104a, at about 99° C. (for example, as a liquid or mixed phase fluid) and leaves the evaporator 104b also at about 99° C. (for example, as a vapor with some superheating).

As shown in FIG. 1TB, as the tube side fluid (for example, the hot oil or water in the heating fluid circuit 105) is circulated through the evaporator 106a, heat is transferred from that fluid to the shell side fluid (for example, the ORC working fluid). Thus, the tube side fluid enters the evaporator 106a at about 160° C. and leaves the evaporator 106a at about 53° C. The shell side fluid enters the evaporator 106a at about 30° C. (for example, as a liquid) and leaves the evaporator 106a at about 99° C. (for example, as a vapor).

As shown in FIG. 1TC, as the tube side fluid (for example, the hot oil or water in the heating fluid circuit 107) is circulated through the evaporator 108a, heat is transferred from that fluid to the shell side fluid (for example, the ORC working fluid). Thus, the tube side fluid enters the evaporator 108a at about 147° C. and leaves the evaporator 108a at about 60° C. The shell side fluid enters the evaporator 108a at about 30° C. (for example, as a liquid) and leaves the evaporator 108a at about 99° C. (for example, as a vapor).

Each of the graphs shown in FIGS. 1TB and 1TC include a "pinch point" for the shell-side fluid (for example, the ORC working fluid). The pinch point, which occurs as the fluid reaches about 99° C., represents the temperature at which the shell-side fluid vaporizes. As the shell-side fluid continues through the respective evaporator, the fluid temperature remains substantially constant (that is, about 99° C.) as the fluid complete vaporizes and, in some aspects, becomes superheated.

Figure 1U:
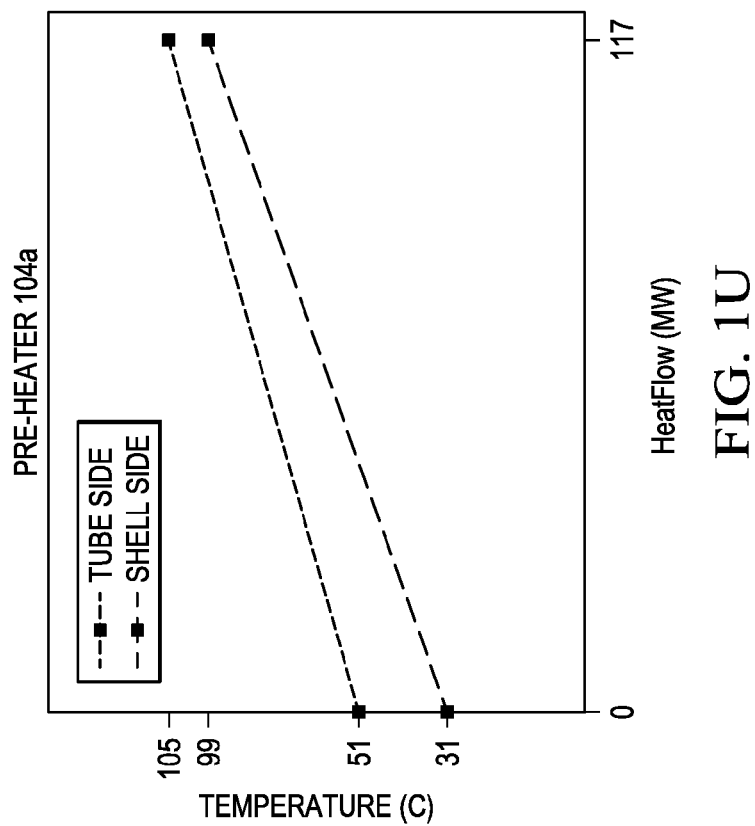
FIG. 1U is a graph that shows a tube side fluid temperature and a shell side fluid temperature in a pre-heater during an operation of the network of FIGS. 1A, 1B, and 1C.
Figure 1T:
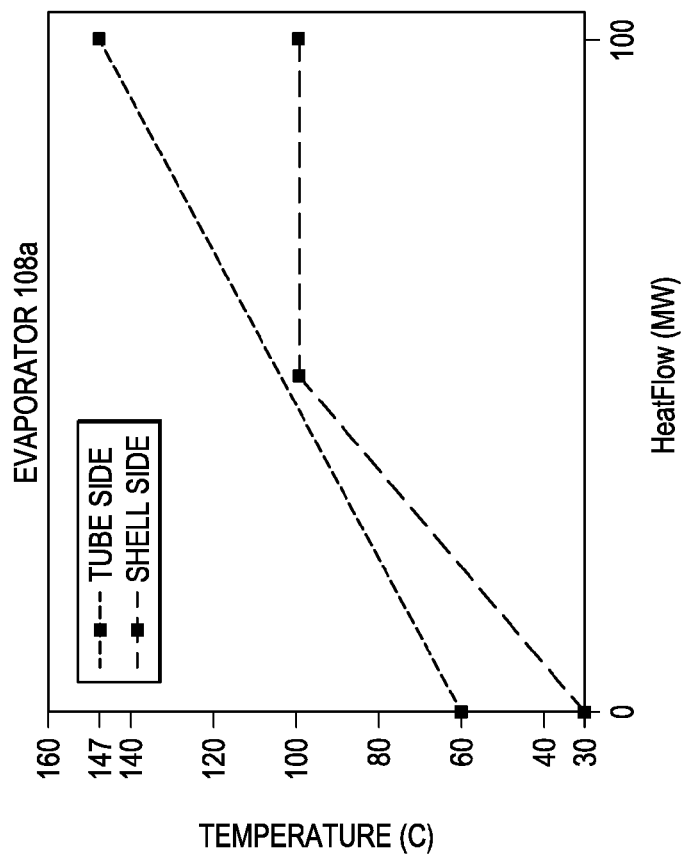

FIG. 1U is a graph that show a tube side fluid temperature (for example, a heating fluid flow) and a shell side fluid temperature (for example, an ORC working fluid flow) in the pre-heater 104a during an operation of the system 100. This graph shows a temperature difference between the fluids on the y-axis relative to a heat flow between the fluids on the x-axis. For example, as shown in this figure, as the temperature difference between the fluids decreases, a heat flow between the fluids can increase. This graph shows a temperature difference between the fluids on the y-axis relative to a heat flow between the fluids on the x-axis. For example, as shown in FIG. 1U, as the tube side fluid (for example, the hot oil or water in the heating fluid circuit 102) is circulated through the pre-heater 104a, heat is transferred from that fluid to the shell side fluid (for example, the ORC working fluid). Thus, the tube side fluid enters the pre-heater 104a at about 105° C. and leaves the pre-heater 104a at about 50° C. The shell side fluid enters the pre-heater 104a at about 30° C. (for example, as a liquid) and leaves the pre-heater 104a at about 99° C. (for example, also as a liquid or mixed phase fluid).

The techniques to recover heat energy generated by a petrochemical refining system described later can be implemented in at least one or both of two example scenarios. In the first scenario, the techniques can be implemented in a petrochemical refining system that is to be constructed. For example, a geographic layout to arrange multiple sub-units of a petrochemical refining system can be identified. The geographic layout can include multiple sub-unit locations at which respective sub-units are to be positioned. Identifying the geographic layout can include actively determining or calculating the location of each sub-unit in the petrochemical refining system based on particular technical data, for example, a flow of petrochemicals through the sub-units starting from crude petroleum and resulting in refined petroleum. Identifying the geographic layout can alternatively or in addition include selecting a layout from among multiple previously-generated geographic layouts. A first subset of sub-units of the petrochemical refining system can be identified. The first subset can include at least two (or more than two) heat-generating sub-units from which heat energy is recoverable to generate electrical power. In the geographic layout, a second subset of the multiple sub-unit locations can be identified. The second subset includes at least two sub-unit locations at which the respective sub-units in the first subset are to be positioned. A power generation system to recover heat energy from the sub-units in the first subset is identified. The power generation system can be substantially similar to the power generation system described earlier. In the geographic layout, a power generation system location can be identified to position the power generation system. At the identified power generation system location, a heat energy recovery efficiency is greater than a heat energy recovery efficiency at other locations in the geographic layout. The petrochemical refining system planners and constructors can perform modeling or computer-based simulation experiments (or both) to identify an optimal location for the power generation system to maximize heat energy recovery efficiency, for example, by minimizing heat loss when transmitting recovered heat energy from the at least two heat-generating sub-units to the power generation system. The petrochemical refining system can be constructed according to the geographic layout by positioning the multiple sub-units at the multiple sub-unit locations, positioning the power generation system at the power generation system location, interconnecting the multiple sub-units with each other such that the interconnected multiple sub-units are configured to refine petrochemicals, and interconnecting the power generation system with the sub-units in the first subset such that the power generation system is configured to recover heat energy from the sub-units in the first subset and to provide the recovered heat energy to the power generation system. The power generation system is configured to generate power using the recovered heat energy.

In the second scenario, the techniques can be implemented in an operational petrochemical refining system. In other words, the power generation system described earlier can be retrofitted to an already constructed and operational petrochemical refining system.

In this manner, a combined power of 75 MW can be obtained from the three power generation systems described here. Implementations of the subject matter described here can increase an energy output of petrochemical refining systems by about 69 MW for local utilization or export to an electricity grid. In this manner, the carbon consumption and GHG emissions of the plant can be decreased.

The invention claimed is:

1. A power generation system comprising:
    a first heating fluid circuit thermally coupled to a plurality of heat sources from a plurality of sub-units of a petrochemical refining system;
    a second heating fluid circuit thermally coupled to the plurality of heat sources from the plurality of sub-units of the petrochemical refining system;
    a third heating fluid circuit thermally coupled to the plurality of sources from the plurality of sub-units of the petrochemical refining system;
    a fourth heating fluid circuit thermally coupled to the plurality of sources from the plurality of sub-units of the petrochemical refining system, wherein the plurality of sub-units comprises a hydrocracking plant, an aromatics plant, and a diesel hydro-treating plant,
        wherein a first subset of the plurality of heat sources comprises a plurality of aromatics plant heat exchangers coupled to streams in the aromatics plant,
        wherein a second subset of the plurality of heat sources comprises a plurality of hydrocracking plant heat exchangers coupled to streams in the hydrocracking plant, and
        wherein a third subset of the plurality of heat sources comprises a plurality of diesel hydro-treating plant heat exchangers coupled to streams in the diesel hydro-treating plant;
    a first power generation system, a second power generation system, and a third power generation system comprising a first organic Rankine cycle (ORC), a second ORC and a third ORC, respectively,
        the first ORC comprising (i) a first working fluid that is thermally coupled to the first heating fluid circuit and the second heating fluid circuit to heat the first working fluid, and (ii) a first expander configured to generate electrical power from the heated first working fluid,
        the second ORC comprising (i) a second working fluid that is thermally coupled to the third heating fluid circuit to heat the second working fluid, and (ii) a second expander configured to generate electrical power from the heated second working fluid, and
        the third ORC comprising (i) a third working fluid that is thermally coupled to the fourth heating fluid circuit, and (ii) a third expander configured to generate electrical power from the heated third working fluid; and
    a control system configured to activate a set of control valves to selectively thermally couple each of the first heating fluid circuit, the second heating fluid circuit, the third heating fluid circuit and the fourth heating fluid circuit to at least a portion of the plurality of heat sources.

2. The system of claim 1, wherein:
    the first working fluid is thermally coupled to the first heating fluid circuit in a first pre-heater of the first ORC and to the second heating fluid circuit in a first evaporator of the first ORC,
    the second working fluid is thermally coupled to the second heating fluid circuit in a second evaporator of the second ORC, and
    the third working fluid is thermally coupled to the third heating fluid circuit in a third evaporator of the third ORC.

3. The system of claim 2, wherein each of the first working fluid, the second working fluid or the third working fluid comprises isobutane.

4. The system of claim 1, wherein the first heating fluid circuit, third heating fluid circuit and the fourth heating fluid circuit are fluidly connected to a first heating fluid tank, and wherein the second heating fluid circuit is fluidly connected to a second heating fluid tank.

5. The system of claim 1, wherein the plurality of heat sources in the first heating fluid circuit are fluidly coupled in parallel, wherein the plurality of heat sources in the second heating fluid circuit are fluidly coupled in parallel, wherein the plurality of heat sources in the third heating fluid circuit are fluidly coupled in parallel, and wherein the plurality of heat sources in the fourth heating fluid circuit are fluidly coupled in parallel.

6. The system of claim 1, wherein:
    each hydrocracking plant heat exchanger comprises a respective stream circulated through the hydrocracking plant and a portion of the heating fluid,
    each aromatics plant heat exchanger comprises a respective stream circulated through the aromatics plant and a portion of the heating fluid, and
    each diesel hydro-treating plant heat exchanger comprises a respective stream circulated through the diesel hydro-treating plant and a portion of the heating fluid.

7. The system of claim 6, wherein:
    the aromatics plant comprises a para-xylene separation unit, and wherein a first aromatics plant heat exchanger in the first heating fluid circuit exchanges heat between an extract column overhead stream in the para-xylene separation unit and a portion of the heating fluid,
a second aromatics plant heat exchanger in the first heating fluid circuit exchanges heat between a PX purification column bottom product stream in the para-xylene separation unit and a portion of the heating fluid,
a third aromatics plant heat exchanger in the first heating fluid circuit exchanges heat between a heavy Raffinate column splitter and a portion of the heating fluid,
a fourth aromatics plant heat exchanger in the first heating fluid circuit exchanges heat between a Raffinate splitter column overhead stream and a portion of the heating fluid,
a fifth aromatics plant heat exchanger in the first heating fluid circuit exchanges heat between a Xylene isomerization reactor outlet stream and a portion of the heating fluid,
a sixth aromatics plant heat exchanger in the first heating fluid circuit exchanges heat between a de-heptanizer column overhead stream in a xylene isomerization de-heptanizer in the aromatics plant and a portion of the heating fluid,
a seventh aromatics plant heat exchanger in the first heating fluid circuit exchanges heat between a benzene column overhead stream in an aromatics benzene extraction unit in the aromatics plant and a portion of the heating fluid,
an eighth aromatics plant heat exchanger in the first heating fluid circuit exchanges heat between an extractive distillation column overhead stream in an aromatics complex extractive distillation column unit in the aromatics plant and a portion of the heating fluid, and
a ninth aromatics plant heat exchanger in the first heating fluid circuit exchanges heat between a Raffinate splitter overhead stream in an aromatics complex raffinate splitter in the aromatics plant and a portion of the heating fluid.

8. The system of claim 7, wherein:
a first aromatics plant heat exchanger in the second heating fluid circuit exchanges heat between a PX purification column overhead stream in the aromatics plant and a portion of the heating fluid, and
a second aromatics plant heat exchanger in the second heating fluid circuit exchanges heat between a Raffinate column overhead stream in the aromatics plant and a portion of the heating fluid.

9. The system of claim 8, wherein:
a first hydrocracking plant heat exchanger in third heating fluid circuit exchanges heat between a $2^{nd}$ stage reaction section feed stream to $2^{nd}$ stage cold high pressure separator in the hydrocracking plant and a portion of the heating fluid,
a second hydrocracking plant heat exchanger in third heating fluid circuit exchanges heat between a $1^{st}$ stage reaction section feed stream to $1^{st}$ stage cold high pressure separator in the hydrocracking plant and a portion of the heating fluid,
a third hydrocracking plant heat exchanger in third heating fluid circuit exchanges heat between a hydrocracking product stripper overhead stream in the hydrocracking plant and a portion of the heating fluid,
a fourth hydrocracking plant heat exchanger in the third heating fluid circuit exchanges heat between a hydrocracking main fractionator overhead stream in the hydrocracking plant and a portion of the heating fluid,
a fifth hydrocracking plant heat exchanger in the third heating fluid circuit exchanges heat between a hydrocracking main fractionator diesel product stream in the hydrocracking plant and a portion of the heating fluid,
a sixth hydrocracking plant heat exchanger in the third heating fluid circuit exchanges heat between a hydrocracking main fractionator kerosene pumparound stream in the hydrocracking plant and a portion of the heating fluid, and
a seventh hydrocracking plant heat exchanger in the third heating fluid circuit exchanges heat between a hydrocracking main fractionator kerosene stream in the hydrocracking plant and a portion of the heating fluid.

10. The system of claim 9, wherein:
a first diesel hydro-treating plant heat exchanger in the fourth heating fluid circuit exchanges heat between a light effluent to cold separator stream in the diesel hydro-treating plant and a portion of the heating fluid,
a second diesel hydro-treating plant heat exchanger in the fourth heating fluid circuit exchanges heat between a diesel stripper overhead stream in the diesel hydro-treating plant and a portion of the heating fluid, and
a third diesel hydro-treating plant heat exchanger in the fourth heating fluid circuit exchanges heat between a diesel stripper product stream in the diesel hydro-treating plant and a portion of the heating fluid.

11. The system of claim 1, wherein the heating fluid circuit comprises water or oil.

12. The system of claim 1, wherein the power generation system is on-site at the petrochemical refining system.

13. The system of claim 1, wherein the power generation system is configured to generate about 69 MW of power.

14. A method of recovering heat energy generated by a petrochemical refining system, the method comprising:
identifying a geographic layout to arrange a plurality of sub-units of a petrochemical refining system, the geographic layout including a plurality of sub-unit locations at which the respective plurality of sub-units are to be positioned, wherein the plurality of sub-units comprises a hydrocracking plant, an aromatics plant and a diesel hydro-treating plant;
identifying a first subset of the plurality of sub-units of the petrochemical refining system, the first subset including a plurality of hydrocracking plant heat exchangers coupled to streams in the hydrocracking plant, a plurality of aromatics plant heat exchangers coupled to streams in the aromatics plant, and a plurality of diesel hydro-treating plant heat exchangers coupled to streams in the diesel hydro-treating plant, wherein heat energy is recoverable from the first subset to generate electrical power;
identifying, in the geographic layout, a second subset of the plurality of sub-unit locations, the second subset including sub-unit locations at which the respective sub-units in the first subset are to be positioned;
identifying a first power generation system, a second power generation system, and a third power generation system comprising a first organic Rankine cycle (ORC), a second ORC and a third ORC, respectively, the first ORC comprising (i) a first working fluid that is thermally coupled to the first heating fluid circuit and the second heating fluid circuit to heat the first working fluid, and (ii) a first expander configured to generate electrical power from the heated first working fluid,
the second ORC comprising (i) a second working fluid that is thermally coupled to the third heating fluid circuit to heat the second working fluid, and (ii) a second expander configured to generate electrical power from the heated second working fluid, and the third ORC comprising (i) a third working fluid that is thermally coupled to the fourth heating fluid circuit, and (ii) a third expander configured to generate electrical power from the heated third working fluid, and a control system configured to activate a set of control valves to selectively thermally couple each of the first heating fluid circuit, the second heating fluid circuit, the third heating fluid circuit and the fourth heating fluid circuit to at least a portion of the plurality of heat sources; and identifying, in the geographic layout, a power generation system location to position each of the first power generation system, the second power generation system, and the third power generation system, wherein a heat energy recovery efficiency at the power generation system location is greater than a heat energy recovery efficiency at other locations in the geographic layout.

15. The method of claim 14, further comprising constructing the petrochemical refining system according to the geographic layout by positioning the plurality of sub-units at the plurality of sub-unit locations, positioning each of the first power generation system, the second power generation system, and the third power generation system at the respective power generation system location, interconnecting the plurality of sub-units with each other such that the interconnected plurality of sub-units are configured to refine petrochemicals, and interconnecting each power generation system with the sub-units in the first subset such that each power generation system is configured to recover heat energy from the sub-units in the first subset and to provide the recovered heat energy to each power generation system, each power generation system configured to generate power using the recovered heat energy.

16. The method of 15, further comprising:
    operating the petrochemical refining system to refine petrochemicals; and
    operating the first power generation system, the second power generation system, and the third power generation system to:
        recover heat energy from the sub-units in the first subset through the first heating fluid circuit, the second heating fluid circuit, the third heating fluid circuit, and the fourth heating fluid circuit;
        provide the recovered heat energy to the first power generation system, the second power generation system, and the third power generation system; and
        generate power using the recovered heat energy.

17. The method of claim 16, further comprising:
    thermally coupling the first working fluid to the first heating fluid circuit in a first pre-heater of the first ORC and to the second heating fluid circuit in a first evaporator of the first ORC,
    thermally coupling the second working fluid to the second heating fluid circuit in a second evaporator of the second ORC, and
    thermally coupling the third working fluid to the third heating fluid circuit in a third evaporator of the third ORC.

18. The method of claim 16, wherein each aromatics plant heat exchanger comprises a respective stream circulated through the aromatics plant and a portion of the heating fluid, and wherein operating the first power generation system, the second power generation system, and the third power generation system comprises:
    operating a first aromatics plant heat exchanger in the first heating fluid circuit to exchange heat between an extract column overhead stream in a para-xylene separation unit in the aromatics plant and a portion of the heating fluid,
    operating a second aromatics plant heat exchanger in the first heating fluid circuit to exchange heat between a PX purification column bottom product stream in the para-xylene separation unit and a portion of the heating fluid,
    operating a third aromatics plant heat exchanger in the first heating fluid circuit to exchange heat between a heavy Raffinate column splitter in the aromatics plant and a portion of the heating fluid,
    operating a fourth aromatics plant heat exchanger in the first heating fluid circuit to exchange heat between a Raffinate splitter column overhead stream in the aromatics plant and a portion of the heating fluid,
    operating a fifth aromatics plant heat exchanger in the first heating fluid circuit to exchange heat between a Xylene isomerization reactor outlet stream in the aromatics plant and a portion of the heating fluid,
    operating a sixth aromatics plant heat exchanger in the first heating fluid circuit to exchange heat between a de-heptanizer column overhead stream in a xylene isomerization de-heptanizer in the aromatics plant and a portion of the heating fluid,
    operating a seventh aromatics plant heat exchanger in the first heating fluid circuit to exchange heat between a benzene column overhead stream in an aromatics benzene extraction unit in the aromatics plant and a portion of the heating fluid,
    operating an eighth aromatics plant heat exchanger in the first heating fluid circuit to exchange heat between an extractive distillation column overhead stream in an aromatics complex extractive distillation column unit in the aromatics plant and a portion of the heating fluid, and
    operating a ninth aromatics plant heat exchanger in the first heating fluid circuit to exchange heat between a Raffinate splitter overhead stream in an aromatics complex raffinate splitter in the aromatics plant and a portion of the heating fluid.

19. The method of claim 18, wherein operating the first power generation system, the second power generation system, and the third power generation system comprises:
    operating a first aromatics plant heat exchanger in the second heating fluid circuit to exchange heat between a PX purification column overhead stream in the aromatics plant and a portion of the heating fluid, and
    operating a second aromatics plant heat exchanger in the second heating fluid circuit to exchange heat between a Raffinate column overhead stream in the aromatics plant and a portion of the heating fluid.

20. The method of claim 19, wherein each hydrocracking plant heat exchanger comprises a respective stream circulated through the hydrocracking plant and a portion of the heating fluid, and wherein operating the first power generation system, the second power generation system, and the third power generation system comprises:
    operating a first hydrocracking plant heat exchanger in third heating fluid circuit to exchange heat between a $2^{nd}$ stage reaction section feed stream to $2^{nd}$ stage cold high pressure separator in the hydrocracking plant and a portion of the heating fluid, operating a second hydrocracking plant heat exchanger in third heating fluid circuit to exchange heat between a $1^{st}$ stage reaction section feed stream to $1^{st}$ stage cold high pressure separator in the hydrocracking plant and a portion of the heating fluid, operating a third hydrocracking plant heat exchanger in third heating fluid circuit to exchange heat between a hydrocracking product stripper overhead stream in the hydrocracking plant and a portion of the heating fluid, operating a fourth hydrocracking plant heat exchanger in the third heating fluid circuit to exchange heat between a hydrocracking main fractionator overhead stream in the hydrocracking plant and a portion of the heating fluid, operating a fifth hydrocracking plant heat exchanger in the third heating fluid circuit to exchange heat between a hydrocracking main fractionator diesel product stream in the hydrocracking plant and a portion of the heating fluid, operating a sixth hydrocracking plant heat exchanger in the third heating fluid circuit to exchange heat between a hydrocracking main fractionator kerosene pump-around stream in the hydrocracking plant and a portion of the heating fluid, and operating a seventh hydrocracking plant heat exchanger in the third heating fluid circuit to exchange heat between a hydrocracking main fractionator kerosene stream in the hydrocracking plant and a portion of the heating fluid.

21. The method of claim 20, wherein each diesel hydro-treating plant heat exchanger comprises a respective stream circulated through the diesel hydro-treating plant and a portion of the heating fluid, and wherein operating the first power generation system, the second power generation system, and the third power generation system comprises:

operating a first diesel hydro-treating plant heat exchanger in the fourth heating fluid circuit to exchange heat between a light effluent to cold separator stream in the diesel hydro-treating plant and a portion of the heating fluid, operating a second diesel hydro-treating plant heat exchanger in the fourth heating fluid circuit to exchange heat between a diesel stripper overhead stream in the diesel hydro-treating plant and a portion of the heating fluid, and operating a third diesel hydro-treating plant heat exchanger in the fourth heating fluid circuit to exchange heat between a diesel stripper product stream in the diesel hydro-treating plant and a portion of the heating fluid.

22. The method of claim 14, further comprising operating the first power generation system, the second power generation system, and the third power generation system to generate about 69 MW of power.

23. A method of re-using heat energy generated by an operational petrochemical refining system, the method comprising:

identifying a geographic layout that comprises an arrangement of a plurality of sub-units of an operational petrochemical refining system, the geographic layout including a plurality of sub-units, each positioned at a respective sub-unit location;

identifying a first subset of the plurality of sub-units of the petrochemical refining system, the first subset including a plurality of aromatics plant heat exchangers coupled to streams in the aromatics plant, a plurality of hydrocracking plant heat exchangers coupled to streams in the hydrocracking plant, and a plurality of diesel hydro-treating plant heat exchangers coupled to streams in the diesel hydro-treating plant, wherein heat energy is recoverable from the first subset to generate electrical power;

identifying, in the geographic layout, a second subset of the plurality of sub-unit locations, the second subset including sub-unit locations at which the respective sub-units in the first subset have been positioned;

identifying a first power generation system, a second power generation system, and a third power generation system comprising a first organic Rankine cycle (ORC), a second ORC and a third ORC, respectively, the first ORC comprising (i) a first working fluid that is thermally coupled to the first heating fluid circuit and the second heating fluid circuit to heat the first working fluid, and (ii) a first expander configured to generate electrical power from the heated first working fluid, the second ORC comprising (i) a second working fluid that is thermally coupled to the third heating fluid circuit to heat the second working fluid, and (ii) a second expander configured to generate electrical power from the heated second working fluid, and the third ORC comprising (i) a third working fluid that is thermally coupled to the fourth heating fluid circuit, and (ii) a third expander configured to generate electrical power from the heated third working fluid, and a control system configured to activate a set of control valves to selectively thermally couple each of the first heating fluid circuit, the second heating fluid circuit, the third heating fluid circuit and the fourth heating fluid circuit to at least a portion of the plurality of heat sources; and identifying, in the geographic layout, a power generation system location to position each of the first power generation system, the second power generation system, and the third power generation system, wherein a heat energy recovery efficiency at the power generation system location is greater than a heat energy recovery efficiency at other locations in the geographic layout.

24. The method of claim 23, further comprising interconnecting the first power generation system, the second power generation system, and the third power generation system with the sub-units in the first subset through the first heating fluid circuit, the second heating fluid circuit, the third heating fluid circuit and the fourth heating fluid circuit such that the power generation system is configured to recover heat energy from the sub-units in the first subset and to provide the recovered heat energy to the first power generation system, the second power generation system, and the third power generation system, the first power generation system, the second power generation system, and the third power generation system configured to generate power using the recovered heat energy.

25. The method of claim 23, further comprising operating the power generation system to:

recover heat energy from the sub-units in the first subset through the first heating fluid circuit, the second heating fluid circuit, the third heating fluid circuit, and the fourth heating fluid circuit;

provide the recovered heat energy to the first power generation system, the second power generation system, and the third power generation system; and generate power using the recovered heat energy.

26. The method of claim 23, wherein each aromatics plant heat exchanger comprises a respective stream circulated through the aromatics plant and a portion of the heating fluid, and wherein operating the first power generation system, the second power generation system, and the third power generation system comprises:

operating a first aromatics plant heat exchanger in the first heating fluid circuit to exchange heat between an extract column overhead stream in a para-xylene separation unit in the aromatics plant and a portion of the heating fluid, operating a second aromatics plant heat exchanger in the first heating fluid circuit to exchange heat between a PX purification column bottom product stream in the para-xylene separation unit and a portion of the heating fluid, operating a third aromatics plant heat exchanger in the first heating fluid circuit to exchange heat between a heavy Raffinate column splitter in the aromatics plant and a portion of the heating fluid, operating a fourth aromatics plant heat exchanger in the first heating fluid circuit to exchange heat between a Raffinate splitter column overhead stream in the aromatics plant and a portion of the heating fluid, operating a fifth aromatics plant heat exchanger in the first heating fluid circuit to exchange heat between a Xylene isomerization reactor outlet stream in the aromatics plant and a portion of the heating fluid, operating a sixth aromatics plant heat exchanger in the first heating fluid circuit to exchange heat between a de-heptanizer column overhead stream in a xylene isomerization de-heptanizer in the aromatics plant and a portion of the heating fluid, operating a seventh aromatics plant heat exchanger in the first heating fluid circuit to exchange heat between a benzene column overhead stream in an aromatics benzene extraction unit in the aromatics plant and a portion of the heating fluid, operating an eighth aromatics plant heat exchanger in the first heating fluid circuit to exchange heat between an extractive distillation column overhead stream in an aromatics complex extractive distillation column unit in the aromatics plant and a portion of the heating fluid, and operating a ninth aromatics plant heat exchanger in the first heating fluid circuit to exchange heat between a Raffinate splitter overhead stream in an aromatics complex raffinate splitter in the aromatics plant and a portion of the heating fluid.

27. The method of claim 26, wherein operating the first power generation system, the second power generation system, and the third power generation system comprises:

operating a first aromatics plant heat exchanger in the second heating fluid circuit to exchange heat between a PX purification column overhead stream in the aromatics plant and a portion of the heating fluid, and operating a second aromatics plant heat exchanger in the second heating fluid circuit to exchange heat between a Raffinate column overhead stream in the aromatics plant and a portion of the heating fluid.

28. The method of claim 27, wherein each hydrocracking plant heat exchanger comprises a respective stream circulated through the hydrocracking plant and a portion of the heating fluid, and wherein operating the first power generation system, the second power generation system, and the third power generation system comprises:

operating a first hydrocracking plant heat exchanger in third heating fluid circuit to exchange heat between a $2^{nd}$ stage reaction section feed stream to $2^{nd}$ stage cold high pressure separator in the hydrocracking plant and a portion of the heating fluid, operating a second hydrocracking plant heat exchanger in third heating fluid circuit to exchange heat between a $1^{st}$ stage reaction section feed stream to $1^{st}$ stage cold high pressure separator in the hydrocracking plant and a portion of the heating fluid, operating a third hydrocracking plant heat exchanger in third heating fluid circuit to exchange heat between a hydrocracking product stripper overhead stream in the hydrocracking plant and a portion of the heating fluid, operating a fourth hydrocracking plant heat exchanger in the third heating fluid circuit to exchange heat between a hydrocracking main fractionator overhead stream in the hydrocracking plant and a portion of the heating fluid, operating a fifth hydrocracking plant heat exchanger in the third heating fluid circuit to exchange heat between a hydrocracking main fractionator diesel product stream in the hydrocracking plant and a portion of the heating fluid, operating a sixth hydrocracking plant heat exchanger in the third heating fluid circuit to exchange heat between a hydrocracking main fractionator kerosene pump-around stream in the hydrocracking plant and a portion of the heating fluid, and operating a seventh hydrocracking plant heat exchanger in the third heating fluid circuit to exchange heat between a hydrocracking main fractionator kerosene stream in the hydrocracking plant and a portion of the heating fluid.

29. The method of claim 28, wherein each diesel hydro-treating plant heat exchanger comprises a respective stream circulated through the diesel hydro-treating plant and a portion of the heating fluid, and wherein operating the first power generation system, the second power generation system, and the third power generation system comprises:

operating a first diesel hydro-treating plant heat exchanger in the fourth heating fluid circuit to exchange heat between a light effluent to cold separator stream in the diesel hydro-treating plant and a portion of the heating fluid, operating a second diesel hydro-treating plant heat exchanger in the fourth heating fluid circuit to exchange heat between a diesel stripper overhead stream in the diesel hydro-treating plant and a portion of the heating fluid, and operating a third diesel hydro-treating plant heat exchanger in the fourth heating fluid circuit to exchange heat between a diesel stripper product stream in the diesel hydro-treating plant and a portion of the heating fluid.

30. The method of claim 29, further comprising operating the first power generation system, the second power generation system, and the third power generation system to generate about 69 MW of power.

* * * * *

UNITED STATES PATENT AND TRADEMARK OFFICE
CERTIFICATE OF CORRECTION

PATENT NO. : 9,816,759 B2
APPLICATION NO. : 15/087503
DATED : November 14, 2017
INVENTOR(S) : Mahmoud Bahy Mahmoud Noureldin, Hani Mohammed Al Saed and Ahmad Saleh Bunaiyan Page 1 of 1

It is certified that error appears in the above-identified patent and that said Letters Patent is hereby corrected as shown below:

In the Claims

Column 27, Line 39, after "of" insert -- claim --

Signed and Sealed this
Fifteenth Day of May, 2018

Andrei Iancu
*Director of the United States Patent and Trademark Office*